(12) United States Patent
Campton et al.

(10) Patent No.: US 9,417,174 B2
(45) Date of Patent: Aug. 16, 2016

(54) TUBE AND FLOAT SYSTEM AND METHODS OF USING THE SAME

(71) Applicant: RareCyte, Inc., Seattle, WA (US)

(72) Inventors: Daniel Campton, Seattle, WA (US); Joshua Nordberg, Bainbridge Island, WA (US); Evan Castiglia, Seattle, WA (US)

(73) Assignee: Rarecyte, Inc., Seattle, WA (US)

( * ) Notice: Subject to any disclaimer, the term of this patent is extended or adjusted under 35 U.S.C. 154(b) by 121 days.

(21) Appl. No.: 14/166,110

(22) Filed: Jan. 28, 2014

(65) Prior Publication Data

US 2014/0219888 A1  Aug. 7, 2014

Related U.S. Application Data

(60) Provisional application No. 61/759,459, filed on Feb. 1, 2013.

(51) Int. Cl.
*G01N 1/34* (2006.01)
*G01N 13/02* (2006.01)
*G01N 15/00* (2006.01)

(52) U.S. Cl.
CPC ........ *G01N 13/02* (2013.01); *G01N 2013/0275* (2013.01); *G01N 2013/0283* (2013.01); *G01N 2015/0003* (2013.01)

(58) Field of Classification Search
CPC .......... G01N 13/02; G01N 2013/0283; G01N 2015/0003; G01N 2013/0275
See application file for complete search history.

(56) References Cited

U.S. PATENT DOCUMENTS

| 4,003,255 | A | * | 1/1977 | Spencer | ................... | G01F 1/20 |
| | | | | | | 137/486 |
| 5,393,674 | A | | 2/1995 | Levine et al. | | |
| 5,560,830 | A | | 10/1996 | Coleman et al. | | |
| 5,736,033 | A | | 4/1998 | Coleman et al. | | |
| 2007/0092971 | A1 | | 4/2007 | Haubert et al. | | |
| 2007/0190584 | A1 | | 8/2007 | Jurgensen et al. | | |
| 2010/0317106 | A1 | * | 12/2010 | Levine | ................. | G01N 33/491 |
| | | | | | | 435/372 |
| 2011/0266206 | A1 | | 11/2011 | Coleman | | |
| 2012/0308447 | A1 | | 12/2012 | Abrahamson | | |
| 2013/0017130 | A1 | * | 1/2013 | Haubert | .............. | B01L 3/50215 |
| | | | | | | 422/533 |

FOREIGN PATENT DOCUMENTS

WO  WO 2011126868 A1 * 10/2011 .......... B01L 3/50215

* cited by examiner

*Primary Examiner* — Jill Warden
*Assistant Examiner* — Julie Tavares
(74) *Attorney, Agent, or Firm* — Olympic Patent Works PLLC

(57) ABSTRACT

This disclosure is directed to systems and methods for analyzing target materials of a suspension include a tube and a float. The float may include expandable portions. The system traps a target analyte between the expandable float and the tube and/or to create a seal between the expandable float and the tube to inhibit fluid from flowing past the expandable float in the tube. The expandable portions may radially expand when exposed to an expanding fluid, such that the expanding fluid is not a naturally-occurring constituent of the suspension; or, the expandable portions may radially expand when a force is exerted upon the expandable portion. A tube may include expandable portions that expand towards the float.

3 Claims, 24 Drawing Sheets

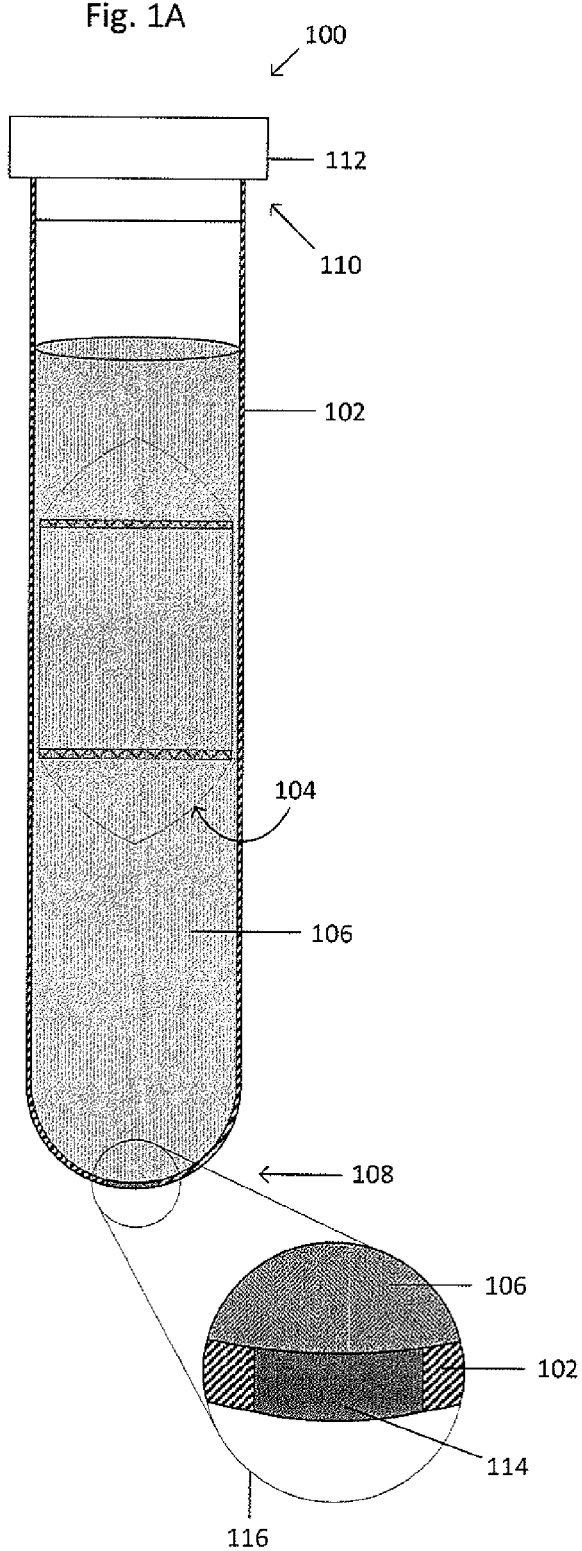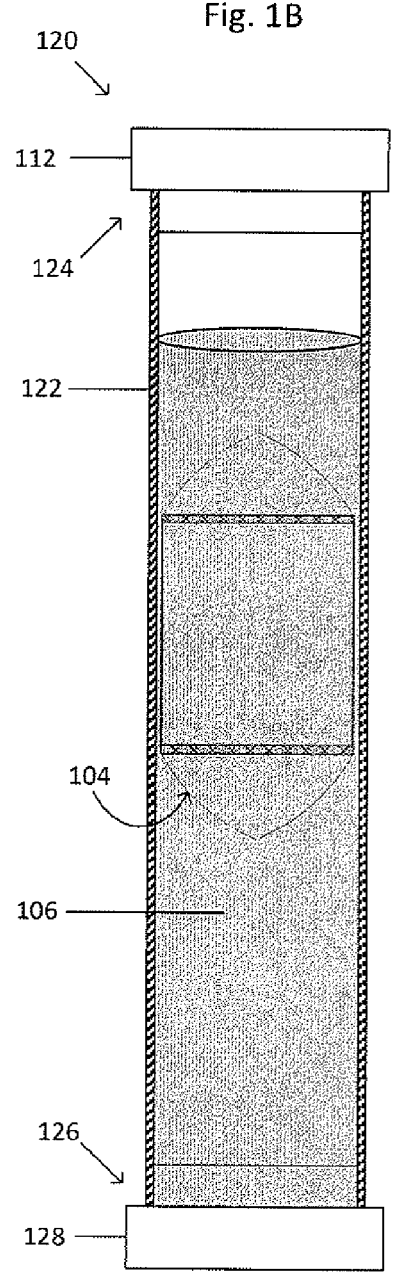
Fig. 1A
Fig. 1B

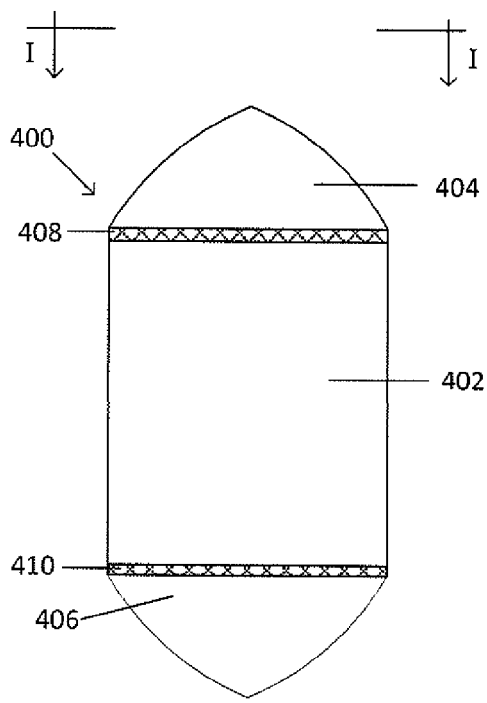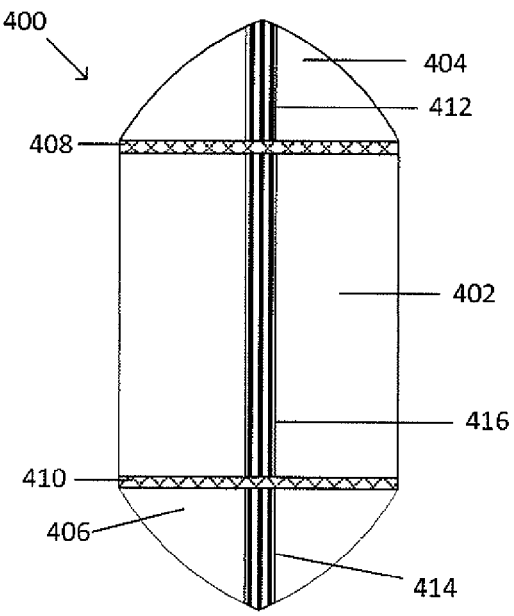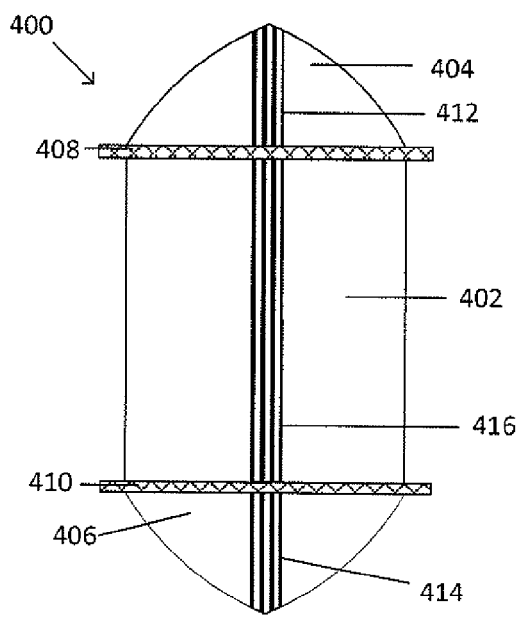

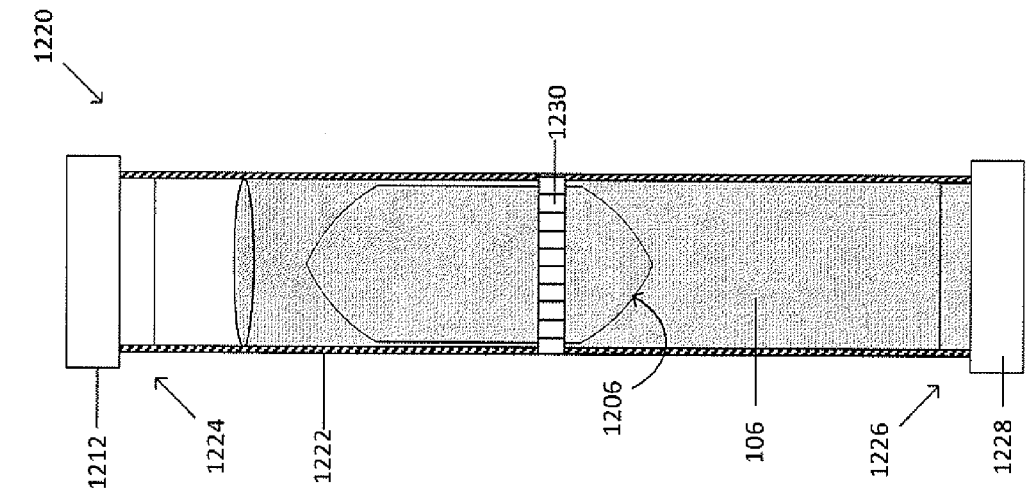
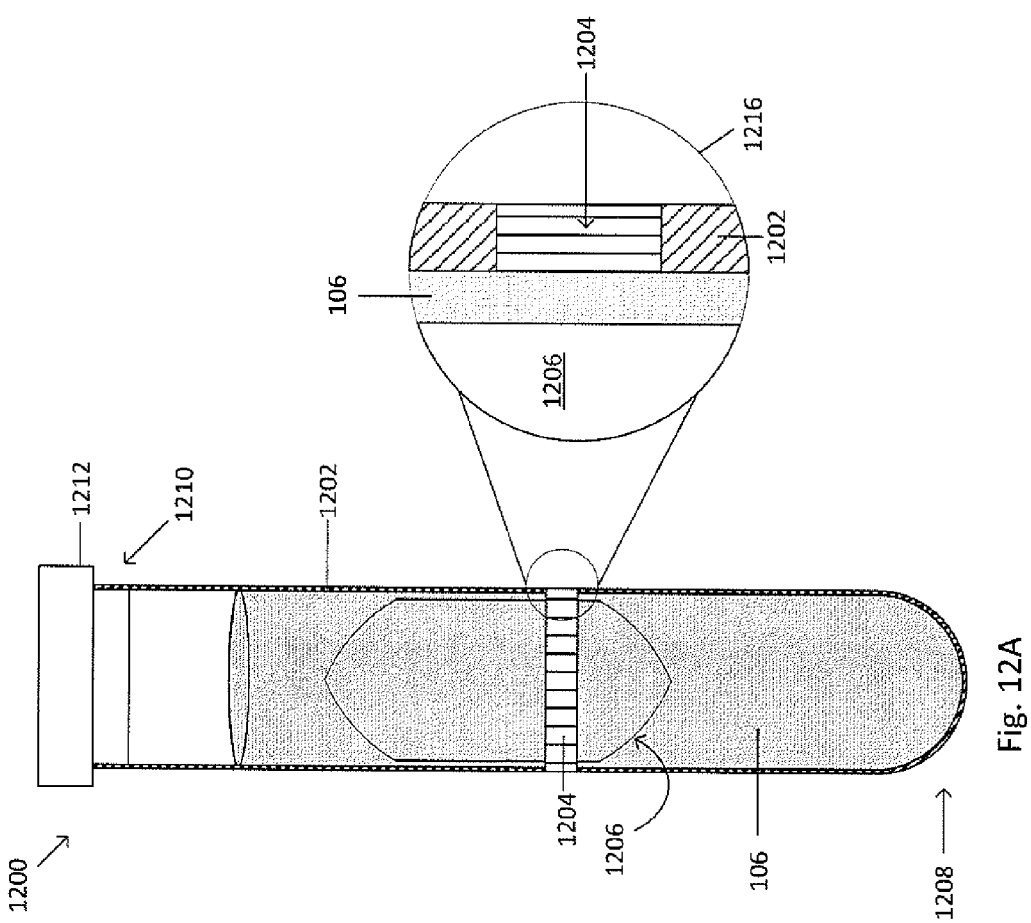
Fig. 12A
Fig. 12B

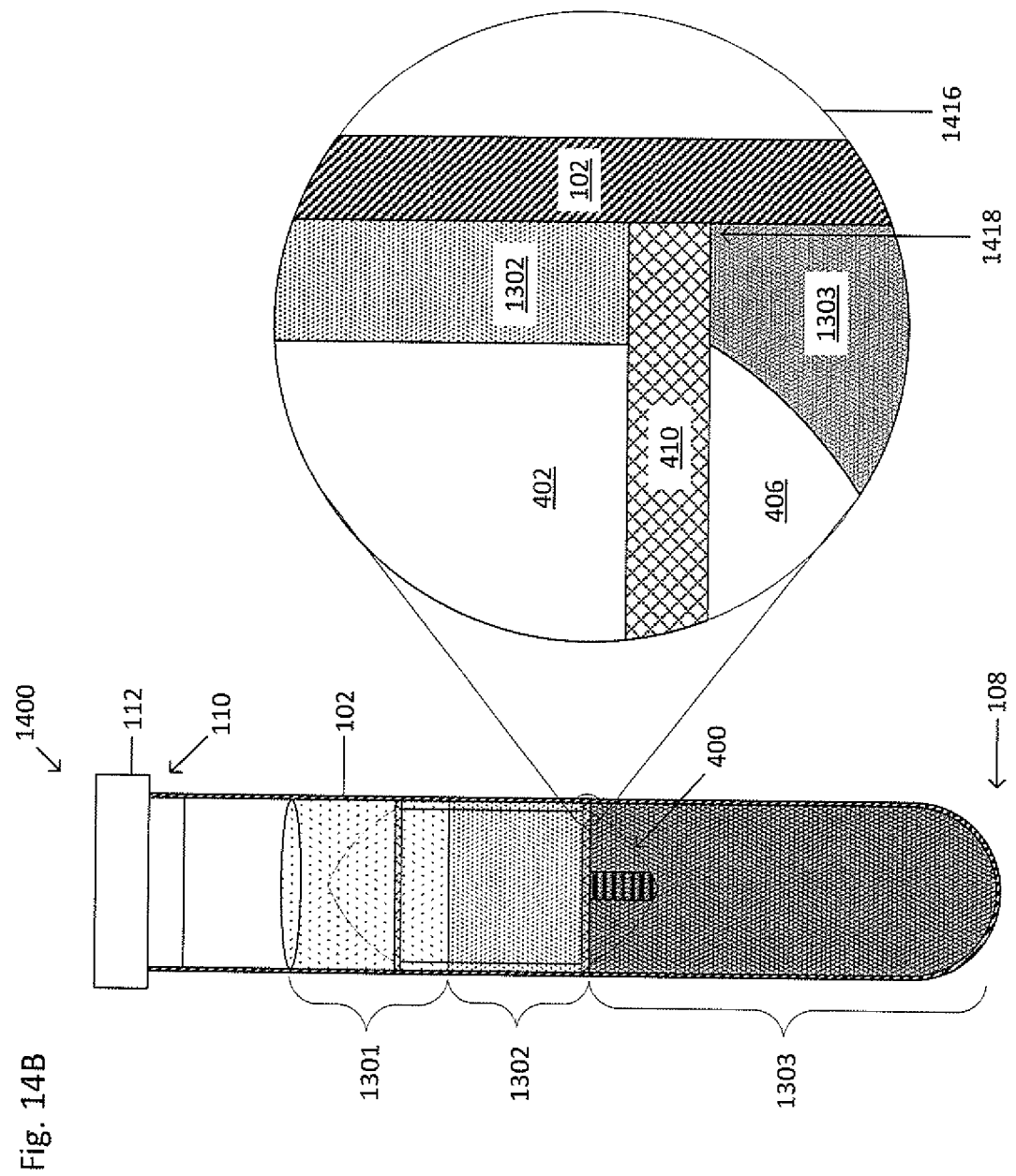

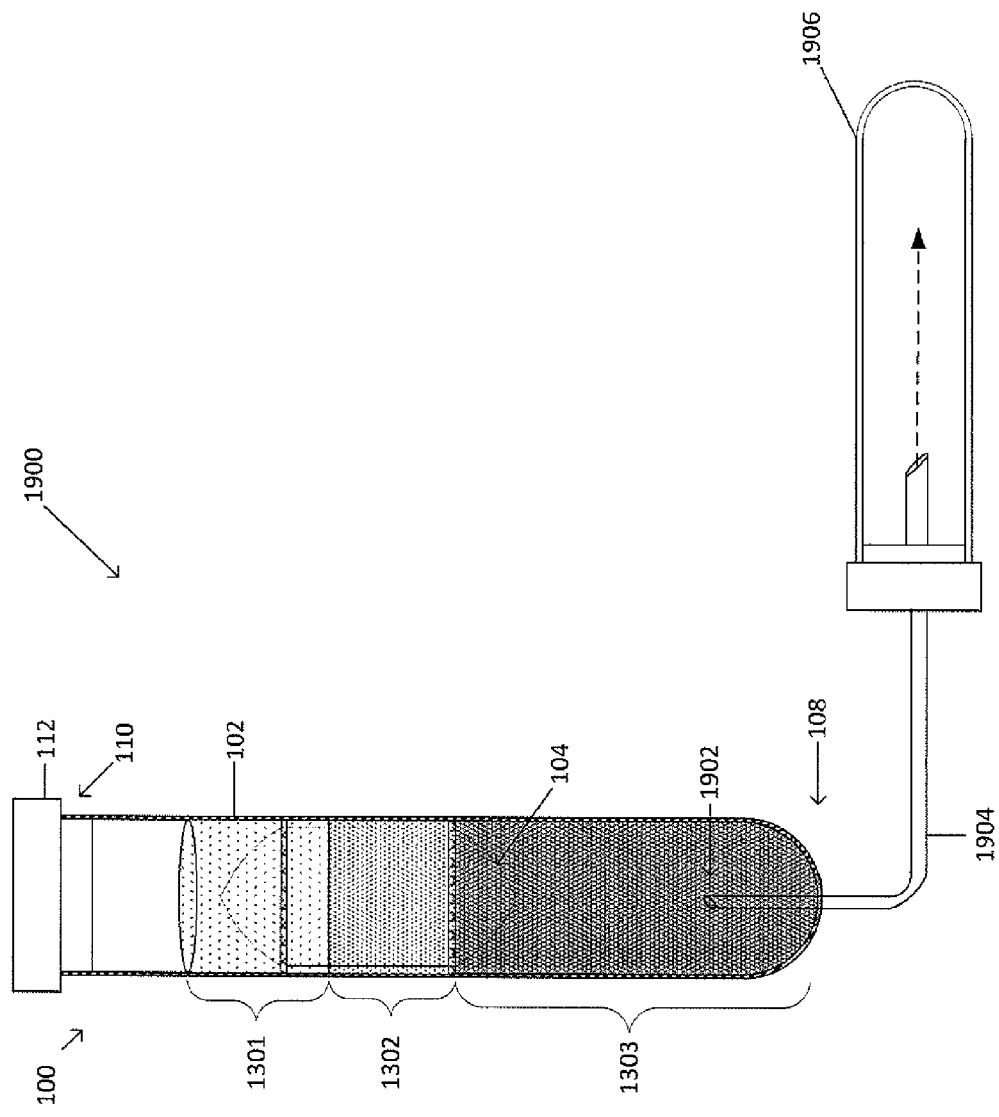

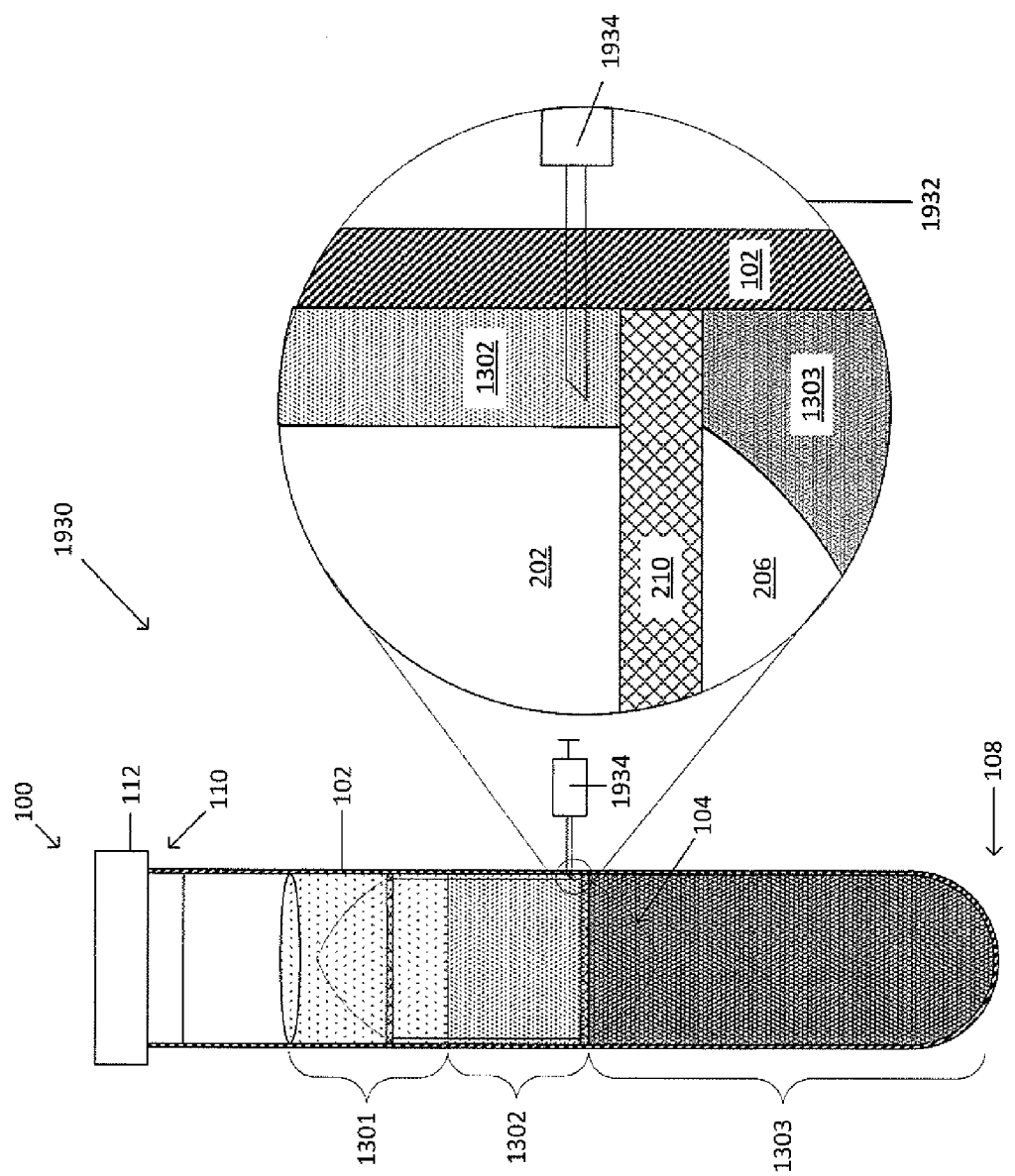

TUBE AND FLOAT SYSTEM AND METHODS OF USING THE SAME

CROSS-REFERENCE TO A RELATED APPLICATION

This application claims the benefit of Provisional Application No. 61/759,495, filed Feb. 1, 2013.

TECHNICAL FIELD

This disclosure relates generally to density-based fluid separation and, in particular, to tube and float systems which expand for the separation and axial expansion of constituent suspension components layered by centrifugation.

BACKGROUND

Suspensions often include materials of interest that are difficult to detect, extract and isolate for analysis. For instance, whole blood is a suspension of materials in a fluid. The materials include billions of red and white blood cells and platelets in a proteinaceous fluid called plasma. Whole blood is routinely examined for the presence of abnormal organisms or cells, such as fetal cells, endothelial cells, epithelial cells, parasites, bacteria, and inflammatory cells, and viruses, including HIV, cytomegalovirus, hepatitis C virus, and Epstein-Barr virus and nucleic acids. Currently, practitioners, researchers, and those working with blood samples try to separate, isolate, and extract certain components of a peripheral blood sample for examination. Typical techniques used to analyze a blood sample include the steps of smearing a film of blood on a slide and staining the film in a way that enables certain components to be examined by bright field microscopy.

On the other hand, materials of interest composed of particles that occur in very low numbers are especially difficult if not impossible to detect and analyze using many existing techniques. Consider, for instance, circulating tumor cells ("CTCs"), which are cancer cells that have detached from a tumor, circulate in the bloodstream, and may be regarded as seeds for subsequent growth of additional tumors (i.e., metastasis) in different tissues. The ability to accurately detect and analyze CTCs is of particular interest to oncologists and cancer researchers, but CTCs occur in very low numbers in peripheral whole blood samples. For instance, a 7.5 ml sample of peripheral whole blood that contains as few as 3 CTCs is considered clinically relevant in the diagnosis and treatment of a cancer patient. However, detecting even 1 CTC in a 7.5 ml blood sample may be clinically relevant and is equivalent to detecting 1 CTC in a background of about 50 billion red and white blood cells. Using existing techniques to find, isolate and extract as few as 3 CTCs of a whole blood sample is extremely time consuming, costly and is extremely difficult to accomplish.

As a result, practitioners, researchers, and those working with suspensions continue to seek systems and methods to more efficiently and accurately detect, isolate and extract target materials of a suspension.

DESCRIPTION OF THE DRAWINGS

FIGS. 1A-1B show isometric views of two example tube and expandable float systems.
FIGS. 4A-4C show an example expandable float.
FIGS. 12A-12B show an example tube with an expandable portion.
FIGS. 14A-14B show an example system including an expandable float.
FIGS. 19A-19D shows example systems for removing a suspension fraction.

DETAILED DESCRIPTION

Figure 2A:
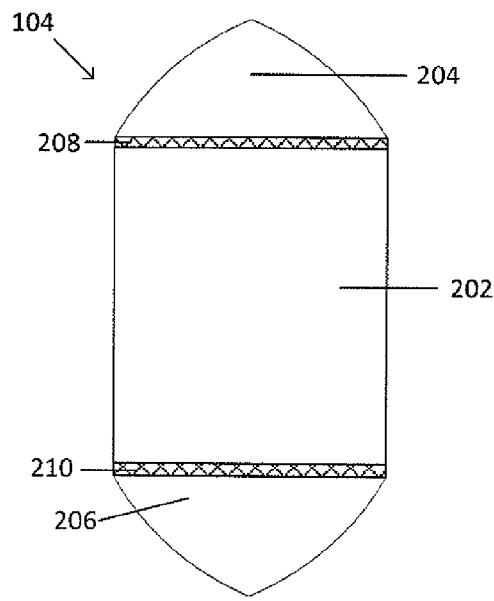
FIGS. 2A-2B show the example expandable float.

This disclosure is directed to systems and methods for analyzing target materials of a suspension include a tube and a float. The float may include expandable portions. The system traps a target analyte between the main body of the expandable float and the tube and/or to create a seal between the expandable float and the tube to inhibit fluid from flowing past the expandable float in the tube. The expandable portions may radially expand when exposed to an expanding fluid, such that the expanding fluid is not a naturally-occurring constituent of the suspension; or, the expandable portions may radially expand when a force is exerted upon the expandable portion. A tube may include expandable portions that expand towards the float.

The detailed description is organized into two subsections: A general description of tube and expandable float systems is provided in a first subsection. Using tube and expandable float systems is provided in a second subsection. The second subsection is broken down even further into trapping/sealing and extraction sub-subsections.

It should be understood that "fluid" may include a gas or a liquid.

General Description of Expandable Systems

FIG. 1A shows an isometric view of an example tube and expandable float system 100. The system 100 includes a tube 102 and an expandable float 104 suspended within a suspension 106. In the example of FIG. 1A, the tube 102 has a circular cross-section, a first closed end 108, and a second open end 110. The open end 110 is sized to receive a stopper or cap 112. The tube may also have two open ends that are sized to receive stoppers or caps, such as the example tube and expandable float system 120 shown FIG. 1B. The system 120 is similar to the system 100 except the tube 102 is replaced by a tube 122 that includes two open ends 124 and 126 configured to receive the cap 112 and a cap 128, respectively. The tubes 102 and 122 have a generally cylindrical geometry, but may also have a tapered geometry that widens, narrows, or a combination thereof toward the open ends 110 and 124, respectively. Although the tubes 102 and 122 have a circular cross-section, in other embodiments, the tubes 102 and 122 can have elliptical, square, triangular, rectangular, octagonal, or any other suitable cross-sectional shape that substantially extends the length of the tube. The tube may also include a plug 114, as shown in magnified view 116, at the closed end 108 to permit the introduction of an expanding fluid, such as by a needle, to radially expand an expandable portion of the expandable float 104; or, to permit the removal of a fluid, the suspension, or a suspension fraction, whether with a syringe, by draining, or the like.

Figure 2B:
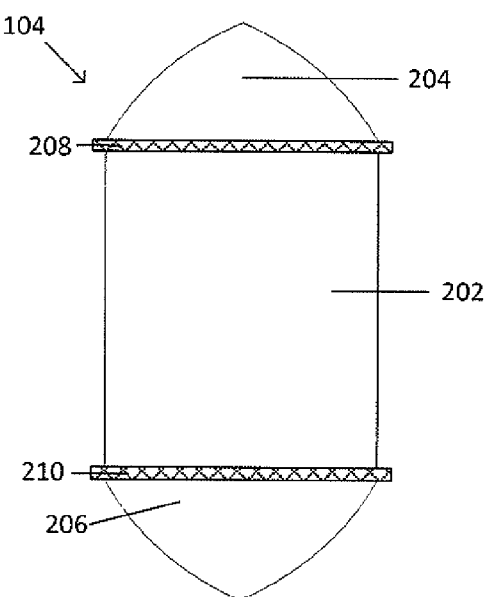

FIG. 2A shows an isometric view of the expandable float 104 shown in FIG. 1. The expandable float 104 includes a main body 202, two teardrop-shaped end caps 204 and 206, and expandable portions 208 and 210, such as an expandable band or a balloon. The expandable float can also include two dome-shaped end caps or two cone-shaped end caps or other appropriate shape. Alternatively, the top end cap and the bottom end cap may be different shapes from one another. The expandable portions 208 and 210 may sit flush with the outer portion of the main body 202. The expandable portions 208 and 210 may be continuous, discontinuous or segmented around the full circumference of the expandable float 104. FIG. 2B shows an isometric view of the expandable float 104 after the expandable portions 208 and 210 has undergone expansion. The expandable portions 208 and 210 do not radially expand from the main body 202 upon the introduction of a naturally-occurring constituent of the suspension. Water, for example, is a naturally-occurring constituent of blood. The expandable portions 208 and 210 can be selectively expandable, such that a naturally-occurring constituent of the suspension 106 does not cause the expandable portions 208 and 210 to expand. When the expandable portions do not expand when introduced to a naturally-occurring constituent of the suspension, an expanding fluid can be introduced to the expandable float 104, such as by directly injecting the expanding fluid into the expandable float 104 or by adding the expanding fluid to the tube prior to or after centrifugation. The expandable portions 208 and 210 and the expanding fluid are complementary in nature, whereby only the expanding fluid is capable of making the expandable portions 208 and 210 expand. The expandable portion 208 and 210 may be located anywhere on the main body of the expandable float or an end cap of the expandable float—for example, but not limited to, proximal to a top end of the expandable float, proximal to a bottom end of the expandable float, substantially at a fraction-fraction interface, or substantially central on the main body of the expandable float.

The expanding fluid may include, but is not limited to, an oil; a non-aqueous fluid (i.e. non-water based); fully-fluorinated fluids, such as perfluoroketones, fluorinated ketones, hydrofluoroethers, hydrofluorocarbons, perfluorocarbons; silicone-based fluids; or the like. When the expandable portion is a balloon, the expanding fluid may be a gas.

Figure 3A:
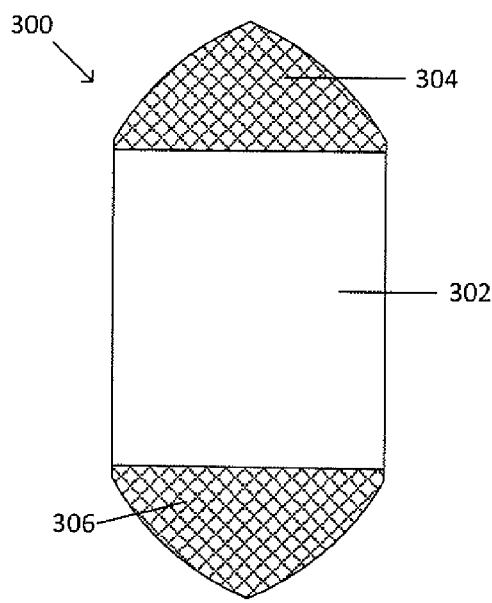
FIGS. 3A-3B show an example expandable float.
Figure 3B:
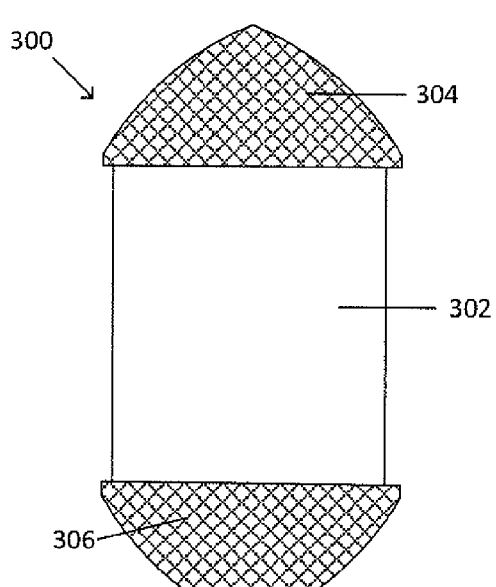

FIG. 3A shows an isometric view of an expandable float 300. The expandable float 300 includes a main body 302 and two teardrop-shaped end caps 304, 306, end caps being expandable. The at least one expandable end cap may be composed entirely of an expandable material, or may be a material discussed below that is overlaid with an expandable material. FIG. 3B shows an isometric view of the expandable float 300 after the end caps 304 and 306 have undergone expansion. The end caps 304 and 306 do not radially expand from the main body 302 upon the introduction of a naturally-occurring constituent of the suspension. The end caps 304 and 306 can be selectively expandable.

FIG. 4A shows an isometric view of an expandable float 400. FIG. 4B shows a cross-sectional view of the expandable float 400 along line I-I. The expandable float 400 may include a central area 412 and 414 that is in fluid communication with an expandable portion 408 and 410, such as an expandable band or a balloon, to permit the introduction of an expanding fluid to the expandable portions 408 and 410. The central area 412 and 414 may include an expandable material or may be a hollow space. A portion of an end cap may be pierceable to permit a needle, syringe, pump, or the like to introduce the expanding fluid into the expandable float. A central area 412 and 414 may be located in a bottom end cap, a top end cap, or both end caps, as shown in FIG. 4B. Additionally, when an expandable float includes at least two expandable portions, an expandable float may also include an extended pore 416 that is in fluid communication with at least two of the expandable portions 408 and 410 to permit the introduction of an expanding fluid to the at least two expandable portions 408 and 410. The central area 412 and 414 and the central pore 416 may include a porous material, an expandable material, such as the expandable material of the expandable portion, or may be a hollow space. The expandable portions 408 and 410 and the central area 412 and 414 may be a singular piece. FIG. 4C shows a cross-sectional view of the expandable float 400 along line I-I after the expandable portions 408 and 410 have undergone expansion.

Figure 5A:
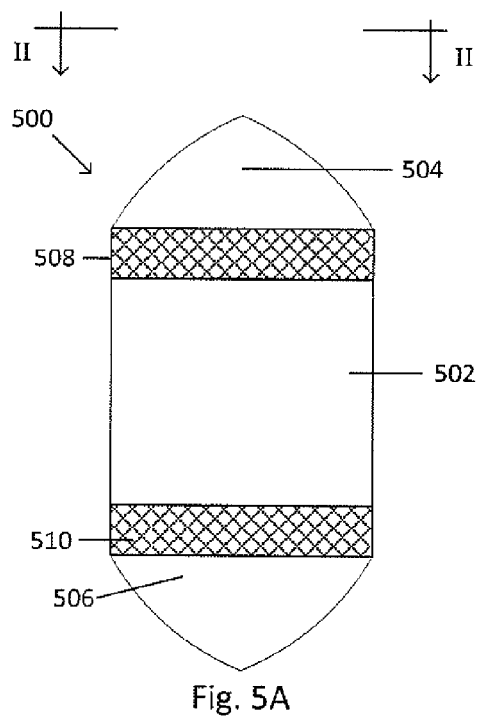
FIGS. 5A-5E show an example expandable float.
Figure 5B:
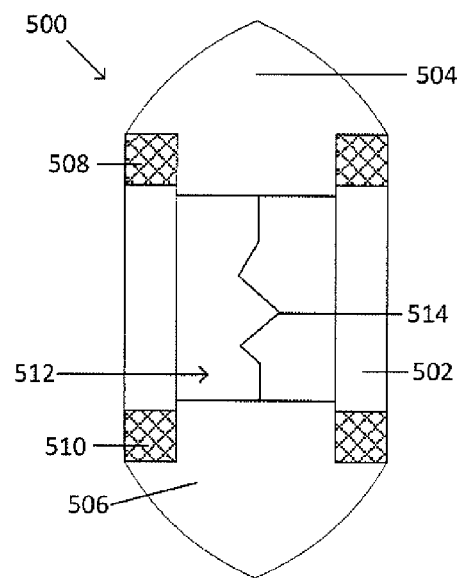

An axial force created internally to the main body may be applied to the expandable portion by the end caps, thereby causing radial expansion of the expandable portion. The internally-created axial force may be applied by magnetic, electrical, or mechanical methods. FIG. 5A shows an isometric view of an expandable float 500. FIG. 5B shows a cross-sectional view of the expandable float 500 along line II-II. The expandable float 500 includes a main body 502, expandable portions 508 and 510, end caps 504 and 506, and a cavity 512 to permit the end caps 504 and 506 to slide, translate, or move partially within the cavity 512, thereby allowing for an axially compressive force to be exerted on the expandable portions 508 and 510 to radially expand the expandable portion 508 and 510. The expandable float 500 may include a notch or a groove (not shown) in the end caps 504 and 506 to push the at least end cap 504 and 506 against the expandable portions 508 and 510, thereby allowing for an axially compressive force to be exerted on the expandable portions 508 and 510 to radially expand the expandable portion 508 and 510. Alternatively, the expandable float 500 may include a trigger 514 to induce end cap translation after a given time has lapsed, after a given event has occurred, or when it is desirous to cause the end cap translation. The trigger 514 may be a spring, a mechanical trigger, a remote trigger, a timed trigger, a semi-solid actuator (i.e. wax), or a primer device. A mechanical trigger can be a device which causes at least one of the end caps to translate toward the center of the expandable float upon the occurrence of a given event. For example, when the expandable float experiences a force of approximately 2500G (where G is the force of gravity), the mechanical trigger activates and causes end cap translation, thereby axially compressing the expandable portion to radially expand the expandable portion. A remote trigger may be a device which is capable of being activated via an external controller, whether that external controller is a computer program or a handheld apparatus. For example, after the expandable float has settled at an appropriate axial location within the tube, an operator or computer program may activate the remote trigger via a handheld apparatus or electronic signal to cause end cap translation, thereby axially compressing the expandable portion to radially expand the expandable portion. A timed trigger may be a device which is capable of activation after a certain time has lapsed. For example, prior to the expandable float being inserted into the tube, a timing trigger can be set to activate at a given time, such as a time slightly after the separation process ends.

Figure 5C:
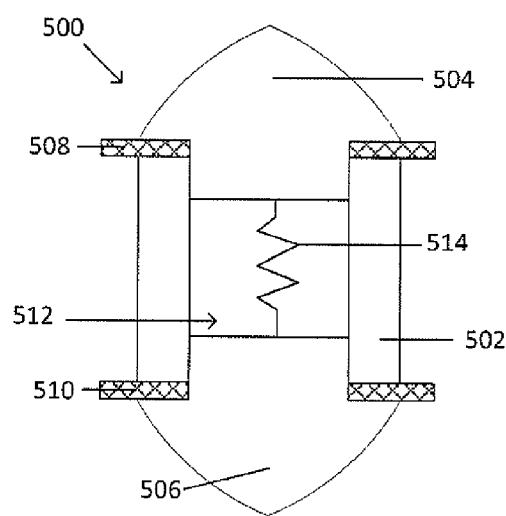

FIGS. 5B and 5C depict a trigger 514 as a primer device in inactive and activated states, respectively. FIG. 5C shows a cross-sectional view of the expandable float 500 along the line II-II after the expandable portions 508 and 510 has undergone expansion. The expandable portions 508 and 510 expand radially due to a force exerted axially on the expandable portions 508 and 510, such as by compression. The primer device is inactive at 1G (where G is the force of gravity); primes the end caps 504 and 506 when the expandable float 500 experiences an increase in forces exerted on the expandable float 500, such as by acceleration during centrifugation, from approximately 1G to a force greater than or equal to 2G; and then, upon decreasing the forces exerted on the expandable float 500, such as by deceleration during centrifugation, activates to move the end caps 504 and 506 within the cavity 512 to cause an axial force, such as by compression, to be exerted on the expandable portions 508 and 510 to radially expand the expandable portions 508 and 510. The primer device may be connected to end caps 504 and 506 and can stretch or start in an extended state during acceleration and then constrict or recoil during deceleration, thereby pulling the end caps 504 and 506 and exerting an axial force on the expandable portion.

Figure 5D:
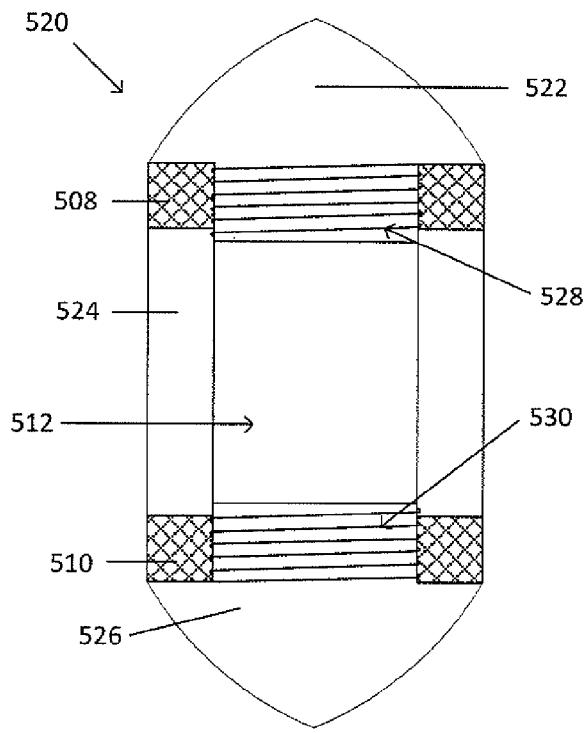
Figure 5E:
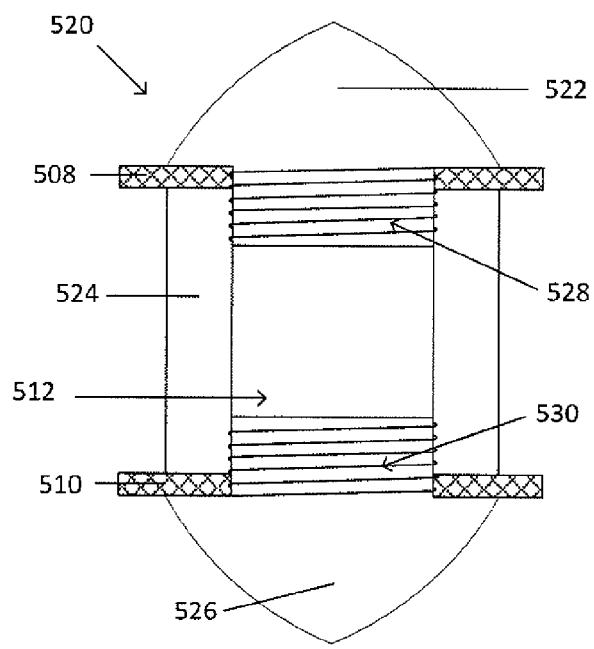

FIG. 5D shows a cross-sectional view of an expandable float 520 in a non-axially compressed state. FIG. 5E shows a cross-sectional view of the expandable float 520 in an axially compressed state. The expandable float 520 is similar to the expandable float 500, except the at least one cap 504 and 506 is replaced with at least one threaded end cap 522 and 526. The at least one threaded end cap 522 and 526 includes threads 528 and 530 to tighten the at least one cap 522 and 526 on an expandable portion 508 and 510, thereby allowing for an axially compressive force to be exerted on the expandable portions 508 and 510 to radially expand the expandable portion 508 and 510. The cavity 512 permits the at least one threaded end cap 522 and 526 to slide, translate, or move partially within the cavity 512, thereby allowing for an axially compressive force to be exerted on the expandable portions 508 and 510 to radially expand the expandable portion 508 and 510.

Figure 6A:
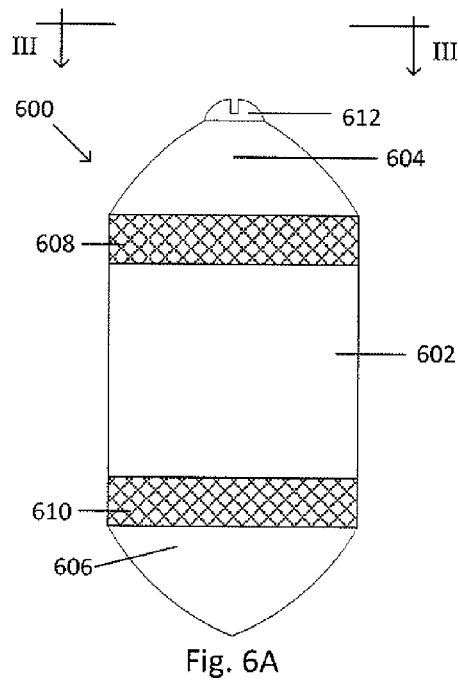
FIGS. 6A-6C show an example expandable float.
Figure 6B:
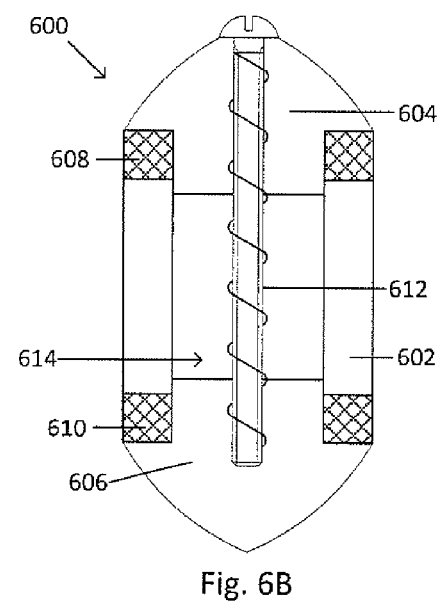
Figure 6C:
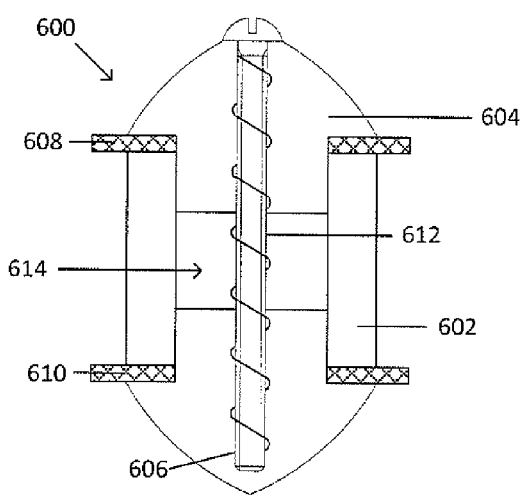

FIG. 6A shows an isometric view of an expandable float 600. FIG. 6B shows a cross-sectional view of the expandable float 600 along line in a non-axially compressed state. FIG. 6C shows a cross-sectional view of the expandable float 600 in an axially compressed state. The expandable float 600 includes a main body 602, expandable portions 608 and 610, end caps 604 and 606, a fastener 612, and a cavity 614. The fastener 612 can be activated, such as by tightening, screwing, pressing, or the like, to cause axial compression of the at least one cap 604 and 606. The axial compression of the end caps 604 and 606 causes the expandable portions 608 and 610 to expand radially. The fastener 612 includes, but is not limited to, a threaded fastener, such as a screw, a rivet, a pin, or the like. The cavity 614 permits the end caps 604 and 606 to slide, translate, or move partially within the cavity 614, thereby allowing for an axially compressive force to be exerted on the expandable portions 608 and 610 to radially expand the expandable portion 608 and 610. The fastener 612 may cause translation of one or two end caps. The fastener 612 may be at or in the top or bottom end cap.

Figure 7:
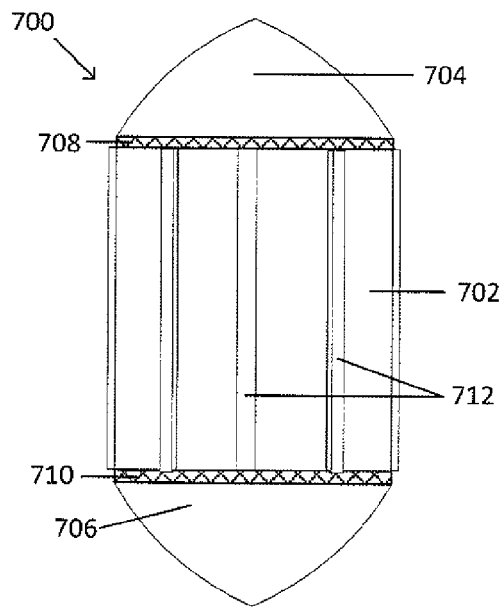
FIGS. 7-11 show example expandable floats.

FIG. 7 shows an isometric view of an expandable float 700. The expandable float 104 includes a main body 702, two teardrop-shaped end caps 704 and 706, expandable portions 708 and 710, such as an expandable band or a balloon, and support members 712 radially spaced and axially oriented on the main body 702. The expandable float can also include two dome-shaped end caps or two cone-shaped end caps. The support members 712 provide a capture engagement with the inner wall of the tube 102.

In alternative embodiments, the number of support members, support member spacing, and support member thickness can each be independently varied. The support members 712 can also be broken or segmented. The main body 702 is sized to have an outer diameter that is less than the inner diameter of the tube 102, thereby defining fluid retention channels between the outer surface of the main body 702 and the inner wall of the tube 102. The surfaces of the main body 702 between the support members 712 can be flat, curved or have another suitable geometry. In the example of FIG. 7, the support members 712 and the main body 702 form a single structure.

Figure 8:
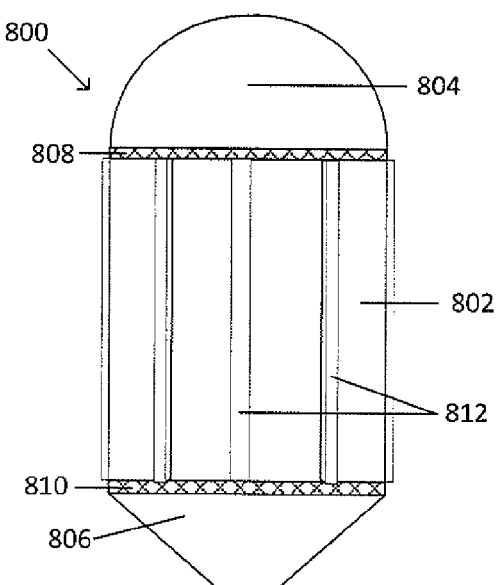

Embodiments include other types of geometric shapes for expandable float end caps. FIG. 8 shows an isometric view of an example expandable float 800 with a dome-shaped end cap 804 and a cone-shaped end cap 806. A main body 802 of the expandable float 800 can include the same structural elements (i.e., support members) 812 as the expandable float 800. An expandable float can also include a teardrop-shaped end cap. The expandable float end caps can include other geometric shapes and are not intended to be limited to the shapes described herein.

Figure 9:
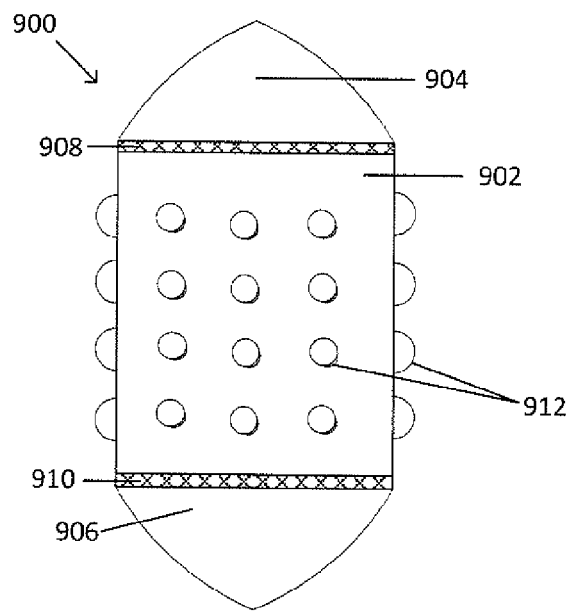
Figure 10:
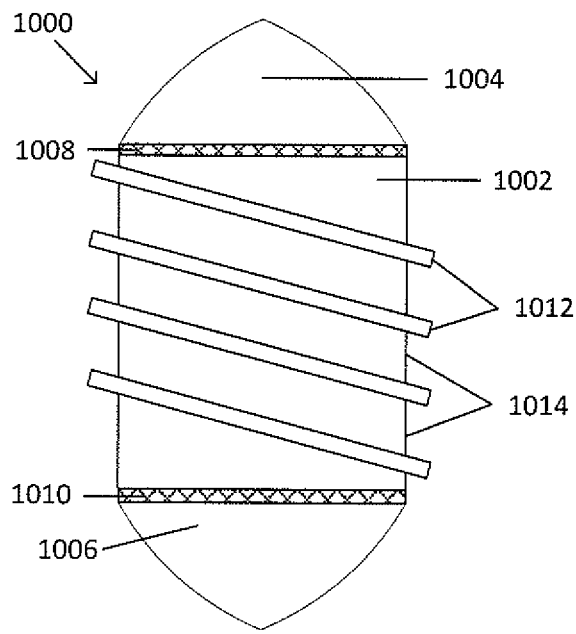
Figure 11:
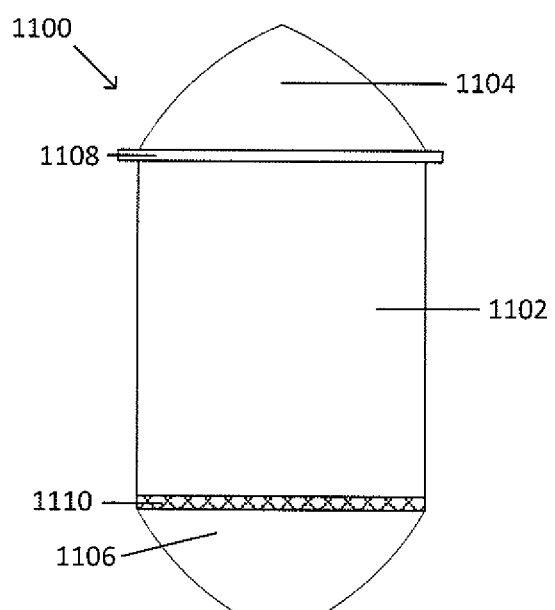

In other embodiments, the main body of the expandable float 600 can include a variety of different support structures for separating target materials, supporting the tube wall, or directing the suspension fluid around the expandable float during centrifugation. FIGS. 9, 10 and 11 show examples of different types of support members. Embodiments are not intended to be limited to these three examples. In FIG. 9, a main body 902 of an expandable float 900 is similar to the expandable float 104 except the main body 902 includes a number of protrusions 912 that provide support for the tube. In alternative embodiments, the number and pattern of protrusions can be varied. In FIG. 10, a main body of an expandable float 1000 includes a single continuous helical structure or ridge 1012 that spirals around the main body 1002 creating a helical channel 1014. In other embodiments, the helical ridge 1012 can be rounded or broken or segmented to allow fluid to flow between adjacent turns of the helical ridge 1014. In various embodiments, the helical ridge spacing and rib thickness can be independently varied. In FIG. 11, a main body 1102 includes a support member 1108 which extends radially from, circumferentially around, and proximal to a top end of the main body 1102. An expandable portion 1110, such as an expandable band or a balloon, is located at proximal to a bottom end of the main body 1102. Alternatively, the expandable portion may be proximal to the top end of the main body and the support member may be proximal to the bottom end of the main body. Alternatively, the expandable portion may be substantially at a fraction-fraction interface. The circumferentially-extending support member may be continuous, segmented, or a discontinuous piece around the main body.

A float, both expandable and non-expandable, can be composed of a variety of different materials including, but not limited to, metals, including, but not limited to, aluminum, brass, gold, silver, tin, copper, bronze, chromium, cobalt, nickel, lead, iron, steel, manganese, zinc, neodymium, and combinations thereof; rigid organic or inorganic materials; ferrous plastics; sintered metal; machined metal; compressible materials, such as compressible polymers; and rigid plastic materials, such as polyoxymethylene ("Delrin®"), polystyrene, acrylonitrile butadiene styrene ("ABS") copolymers, aromatic polycarbonates, aromatic polyesters, carboxymethylcellulose, ethyl cellulose, ethylene vinyl acetate copolymers, nylon, polyacetals, polyacetates, polyacrylonitrile and other nitrile resins, polyacrylonitrile-vinyl chloride copolymer, polyamides, aromatic polyamides ("aramids"), polyamide-imide, polyarylates, polyarylene oxides, polyarylene sulfides, polyarylsulfones, polybenzimidazole, polybutylene terephthalate, polycarbonates, polyester, polyester imides, polyether sulfones, polyetherimides, polyetherketones, polyetheretherketones, polyethylene terephthalate, polyimides, polymethacrylate, polyolefins (e.g., polyethylene, polypropylene), polyallomers, polyoxadiazole, polyparaxylene, polyphenylene oxides (PPO), modified PPOs, polystyrene, polysulfone, fluorine containing polymer such as polytetrafluoroethylene, polyurethane, polyvinyl acetate, polyvinyl alcohol, polyvinyl halides such as polyvinyl chloride, polyvinyl chloride-vinyl acetate copolymer, polyvinyl pyrrolidone, polyvinylidene chloride, specialty polymers, polystyrene, polycarbonate, polypropylene, acrylonitrile butadiene-styrene copolymer, butyl rubber, ethylene propylene diene monomer, others, and combinations thereof.

The expandable portions may constrict to a diameter that is less than a diameter when the expandable portions are fully expanded. For example, the expandable portions may constrict back to an initial diameter (i.e. the "initial diameter" is the diameter of the expandable portions before expansion) by reversing a mechanism by which the expandable portions were initially expanded, such as by removing the expansion fluids or by removing the mechanical force, by introducing a constriction fluid (i.e. a fluid to reverse the effects of the expanding fluid), by puncturing the expandable portions, by introducing at least one form of energy, or by any appropriate mechanism for constricting the expandable portions.

FIG. 12A shows an isometric view of an example tube and float system 1200. The system 1200 includes a tube 1202 and a float 1206 suspended within a suspension 106. In the example of FIG. 12A, the tube 1202 has a circular cross-section, a first closed end 1208, and a second open end 1210. The open end 1210 is sized to receive a stopper or cap 1212. The tube 1202 also includes an expandable portion 1204. The tube may also have two open ends that are sized to receive stoppers or caps, such as the example tube and float system 1220 shown FIG. 12B. The system 1220 is similar to the system 1200 except the tube 1202 is replaced by a tube 1222 that includes two open ends 1224 and 1226 configured to receive the cap 1212 and a cap 1228, respectively. The tube 1222 also includes an expandable portion 1230. The tubes 1202 and 1222 have a generally cylindrical geometry, but may also have a tapered geometry that widens, narrows, or a combination thereof, toward the open ends 1210 and 1224, respectively. Although the tubes 1202 and 1222 have a circular cross-section, in other embodiments, the tubes 1202 and 1222 can have elliptical, square, triangular, rectangular, octagonal, or any other suitable cross-sectional shape that substantially extends the length of the tube. The float 1206 may not include any external features (i.e. support members or expandable portions) or may be configured in a manner similar to other floats discussed herein (i.e. support members and/or expandable portion). The tubes 1202 and 1222 can be composed of a transparent or semitransparent flexible material, such as flexible plastic or another suitable material. The tube may also include a plug (not shown) at the closed end 1208 to permit the removal of a fluid, the suspension, or a suspension fraction, whether with a syringe, by draining, or the like.

FIG. 12A also includes a magnified view 1216 of the expandable portion 1204 in the tube 1202. The expandable portion 1204 may be embedded within the sidewall of the tube 1202; or, the expandable portion 1204 may line the inside of the sidewall of the tube 1202. The expandable portion 1204 may extend the full circumference of the tube 1202, may be segmented along the circumference of the tube 1202, may be located at different points along the circumference and/or the length of the tube 1202, or may only be located at one point within the tube 1202. The expandable portion 1204 of the tube 1202 expands inwardly, thereby reducing an inner diameter of the tube 1202 at the location of the expandable portion 1204 from a first inner diameter to a second inner diameter, such that the second inner diameter is smaller than the first inner diameter.

When an expandable portion is an expandable band, the expandable band can be composed of a material capable of expanding when introduced to a fluid by absorbing at least a portion of the fluid. The expandable material may include, but is not limited to, polymers, elastomers, and gels. The expandable material can be selectively expandable, such that a naturally-occurring constituent of a suspension does not cause the expandable material to expand. An expanding fluid can therefore be introduced to the expandable material to radially expand the expandable material. The expandable material and the expanding fluid are complementary in nature, whereby only the expanding fluid is capable of making the expandable material radially expand. Using a selectively expandable material prevents expanding in undesirable situations and causing the expandable float to become unnecessarily captured within a tube. The selectively expandable material permits the expandable float to first settle in a proper location, then causing the at least one expandable band to expand, thereby trapping the expandable float in an appropriate location within the tube. Alternatively, when the expandable portion is a balloon, the balloon expands and retains an expanding fluid when an expanding fluid is introduced into the expandable portion. As a balloon, the expandable portion does not need to absorb the expanding fluid in a manner similar to that of the expandable material, but may rather retain the expanding fluid and expand appropriately. The balloon may include, but is not limited to, polymers, elastomers, and gels.

Alternatively, the expandable portion may also be any material which is expandable through a conversion process (i.e. photo-convertible) or activation process. When the expandable portion comprises a convertible material or an activatable material, the expandable portion expands in response to energy emitted from a given source to trigger a reaction, thereby causing the material to reach a functional state. The energy includes, but is not limited to, optical energy, thermal energy, chemical energy, electrical energy, electrochemical energy, electromagnetic energy, and sound energy. Alternatively, the expandable portion may also be any material which is expandable through an activation process, such as a piezoelectric material which produces a mechanical strain by an applied electric potential, such as when connected to a battery or other power source via respective leads. Alternatively, the expandable portions may be composed of a shape metal alloy.

It should be further noted that a main body of an expandable float may include an expandable portion comprising an expandable material. The expandable portion may form the entire main body, such that the entire main body can expand, or a segment of the main body, such that a section of the main body can expand.

Furthermore, the expandable portion may not expand radially upon the application of centrifugal force. The top and bottom end caps may not collapse towards the main body due to differences in density during centrifugation. To expand, the expandable portion may be activated in any number of ways, including, but not limited to, the introduction of a solution;

the collapsing of the top and bottom end caps by screwing, triggering, or the like; and the introduction of energy for activation.

The end caps may be manufactured as a portion of the main body, thereby being one singular structure, by machining, injection molding, additive techniques, or the like; or, the end caps may be connected to the main body by a press fit, an adhesive, a screw, any other appropriate method by which to hold at least two pieces together, or combinations thereof.

A tube can be composed of a transparent or semitransparent material. The tube can be flexible or rigid. The tube can be composed of a variety of different materials including, but not limited to, glass; a rigid organic or inorganic materials; and rigid plastic materials, such as polyoxymethylene ("Delrin"), polystyrene, acrylonitrile butadiene styrene ("ABS") copolymers, aromatic polycarbonates, aromatic polyesters, carboxymethylcellulose, ethyl cellulose, ethylene vinyl acetate copolymers, nylon, polyacetals, polyacetates, polyacrylonitrile and other nitrile resins, polyacrylonitrile-vinyl chloride copolymer, polyamides, aromatic polyamides ("aramids"), polyamide-imide, polyarylates, polyarylene oxides, polyarylene sulfides, polyarylsulfones, polybenzimidazole, polybutylene terephthalate, polycarbonates, polyester, polyester imides, polyether sulfones, polyetherimides, polyetherketones, polyetheretherketones, polyethylene terephthalate, polyimides, polymethacrylate, polyolefins (e.g., polyethylene, polypropylene), polyallomers, polyoxadiazole, polyparaxylene, polyphenylene oxides (PPO), modified PPOs, polystyrene, polysulfone, fluorine containing polymer such as polytetrafluoroethylene, polyurethane, polyvinyl acetate, polyvinyl alcohol, polyvinyl halides such as polyvinyl chloride, polyvinyl chloride-vinyl acetate copolymer, polyvinyl pyrrolidone, polyvinylidene chloride, specialty polymers, polystyrene, polycarbonate, polypropylene, acrylonitrite butadiene-styrene copolymer, styrene-butadiene copolymer (i.e. K-Resin®), butyl rubber, ethylene propylene diene monomer, others, and combinations thereof.

The plug can be composed of re-sealable rubber or other suitable re-sealable material that can be repeatedly punctured with a needle or other sharp implement to access the contents of the tube 102 interior and re-seals when the needle or implement is removed. The plug can be formed in the openings and/or the bottom interior of the tube using heated liquid rubber that can be shaped and hardens as the rubber cools. The adhesive used to attach a plug to the wall of the opening and tube interior and can be a polymer-based adhesive, an epoxy, a contact adhesive or any other suitable material for bonding rubber to plastic.

Methods for Using Tube and Expandable Float Systems

I. Sealing/Trapping

A suspension 106 suspecting of containing a target analyte is introduced into a tube 102 of a tube and expandable float system. A solution containing a fluorescent marker may be used to label the target analyte, thereby providing a fluorescent signal for identification and characterization. The target analyte of the suspension 106 may also be labeled prior to introduction into the tube 102. When the target analyte has not been labeled prior to introduction to the tube 102, the contents of the tube 102 are mixed by shaking, swirling, rocking, inversion, rotating, vortex mixing, or stirring. The mixing may be done manually or with the aid of a machine, instrument, or the like. After mixing and conjugating, the expandable float is added to the tube 102. The system then undergoes density-based separation, such as by centrifugation, thereby permitting separation of the suspension into density-based fractions along an axial position in the tube 102 based on density.

Suppose, for example, the suspension includes three fractions, as shown in FIGS. 13A to 19D. During centrifugation, the suspension may be divided into and settle into the three fractions, including a high density fraction 1303, a medium density fraction 1302, and a low density fraction 1301. The expandable float may have any appropriate density to settle in a desired position. The expandable float may settle within the tube 102 at the same axial position as that of the target analyte when the density of the expandable float is selected to be substantially the same as the density of the target analyte. Alternatively, the expandable float may have a density substantially between the densities of the densest fraction 1303 and the medium density fraction 1302. When the density of the expandable float 104 is selected to be substantially between the densities of the densest fraction 1303 and the medium density fraction 1302, the expandable float may be capable of forming a seal with a sidewall of the tube 102, thereby preventing fluids from flowing past the expandable float within the tube 102. The target analyte can be trapped within an analysis area between the expandable float 104 and the tube 102. The analysis area may then be imaged. Alternatively, the expandable float may be pushed into an appropriate position before the expandable float undergoes expansion.

Figure 13A:
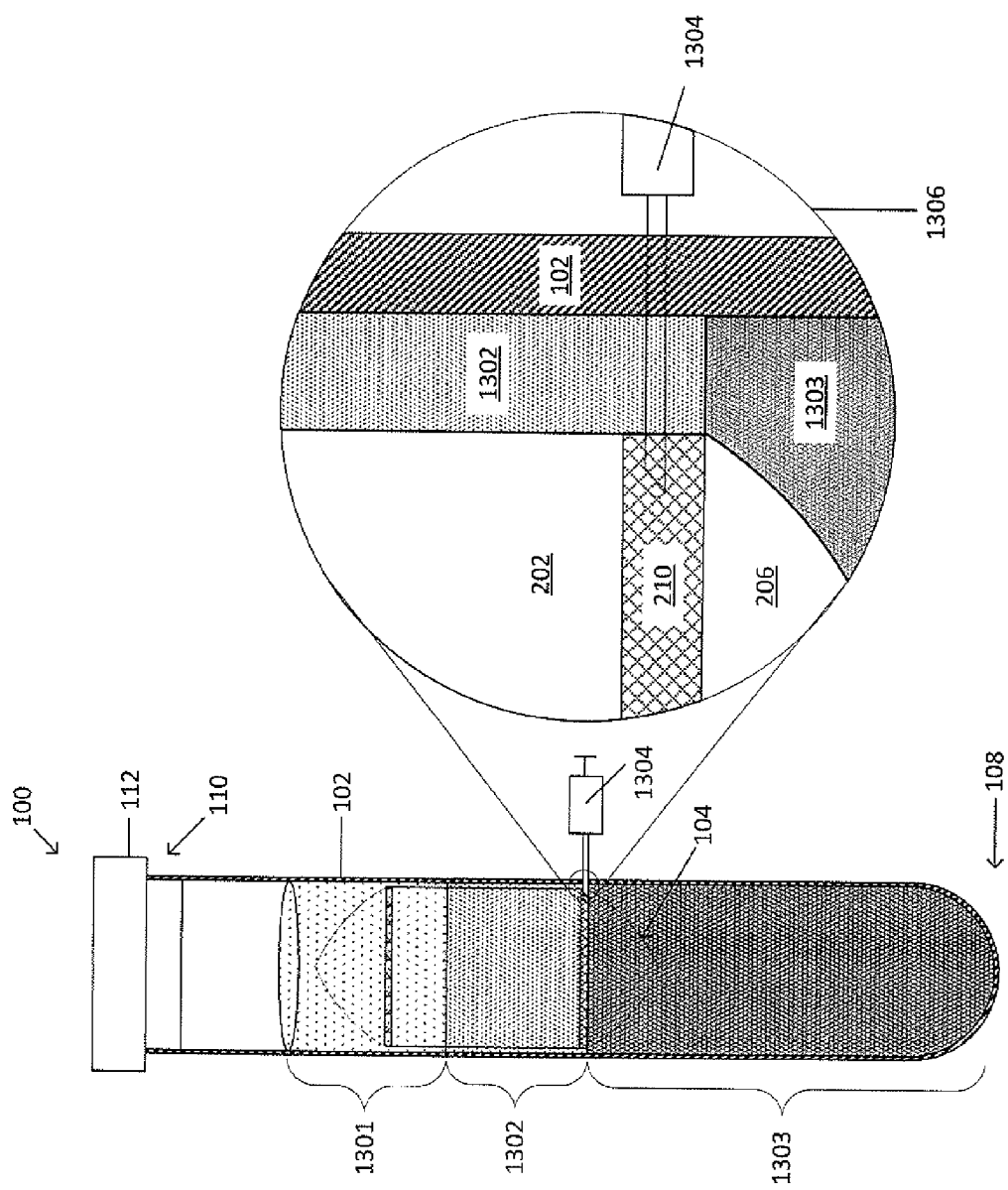
FIGS. 13A-13B show an example system including an expandable float.

Referring now to FIG. 13A, an isometric view of the tube and expandable float system 100 having undergone density-based separation, such as by centrifugation, is shown. After centrifugation, the expandable float 104 settles within the fractions 1301-1303 based on the density of the expandable float 104 relative to the respective densities of the fractions 1301-1303. For example, the expandable float 104 has a density that causes the expandable portion 210 to settle on top of the densest fraction 1303. To form a seal or trap the target analyte, an expanding fluid may be introduced to the expandable portion 210, thereby causing the expandable portion 210 to radially expand to the sidewall of the tube 102. Snapshot 1306 shows a syringe 1304 being used to introduce an expanding fluid to an expandable portion 210 of the expandable float 104. The syringe 1304 can be used to introduce the expanding fluid into the expandable portion 210 of the expandable float 104 through a sidewall of the tube 102. The syringe 1304 may be inserted into the expandable portion 210 of the expandable float 104 through the sidewall of the tube 102 by piercing, creating an opening in the sidewall and inserting the syringe 1304, or the like. The syringe 1304, may, alternatively be a pump. When a pump is used, the pump may be controlled by a program to determine flow rate of the expanding liquid into the tube and expandable float system.

Figure 13B:
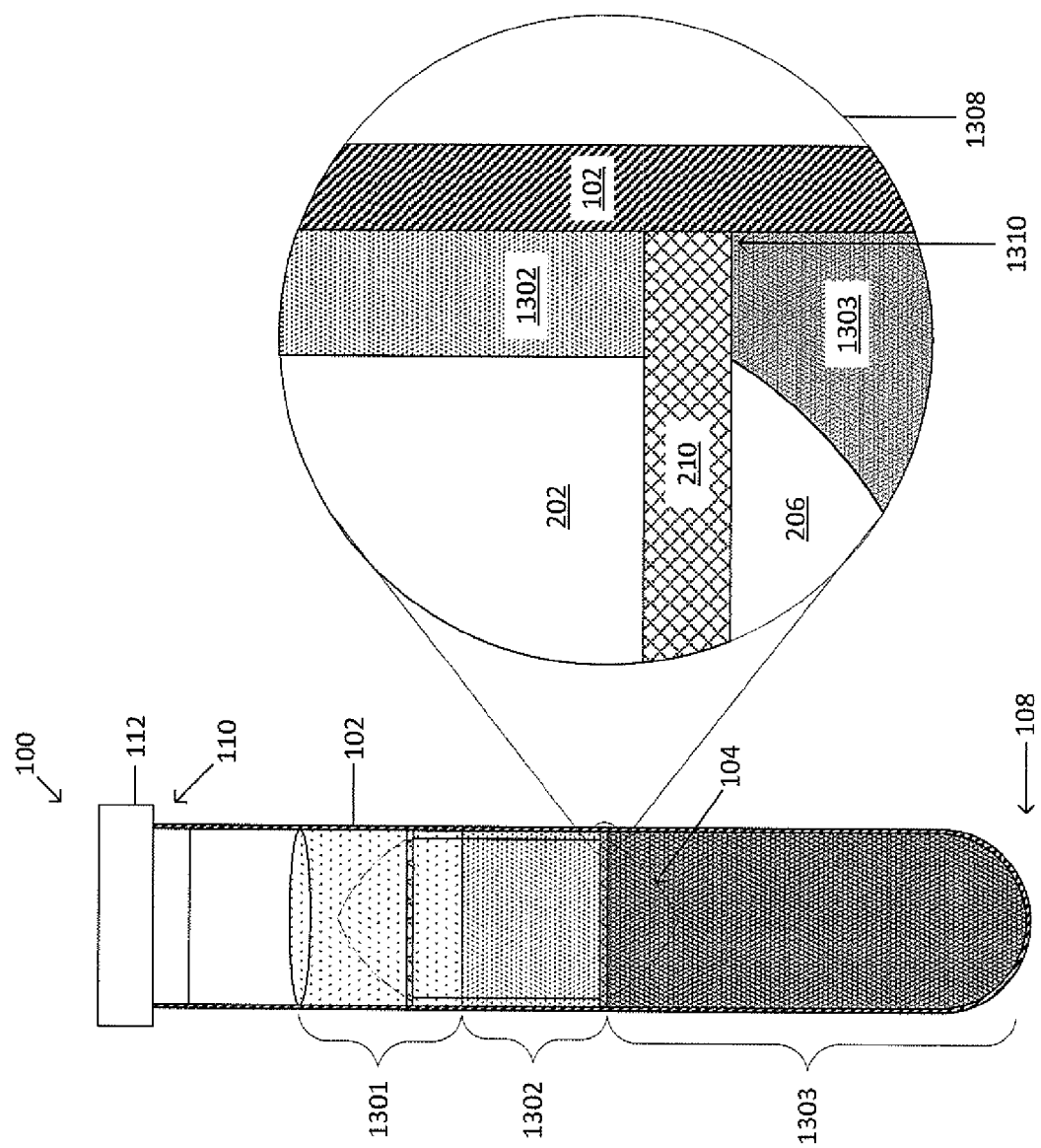

As shown in FIG. 13B, the expandable portion 210, being made of an expandable material, radially expands by absorbing the expanding fluid. The expandable material of the expandable portion 210 absorbs the expanding liquid introduced by the syringe 1304, thereby radially expanding towards the sidewall of the tube 102. The expandable portion 210 can form a seal 1310 with the tube 102 or can trap the target analyte between the expandable float 104 and the tube 102. The seal 1310 can prevent fractions 1302, 1303 from contacting each other. The seal 1310 may also inhibit fluids from flowing past the expandable float 104 in the tube 102.

Figure 14A:
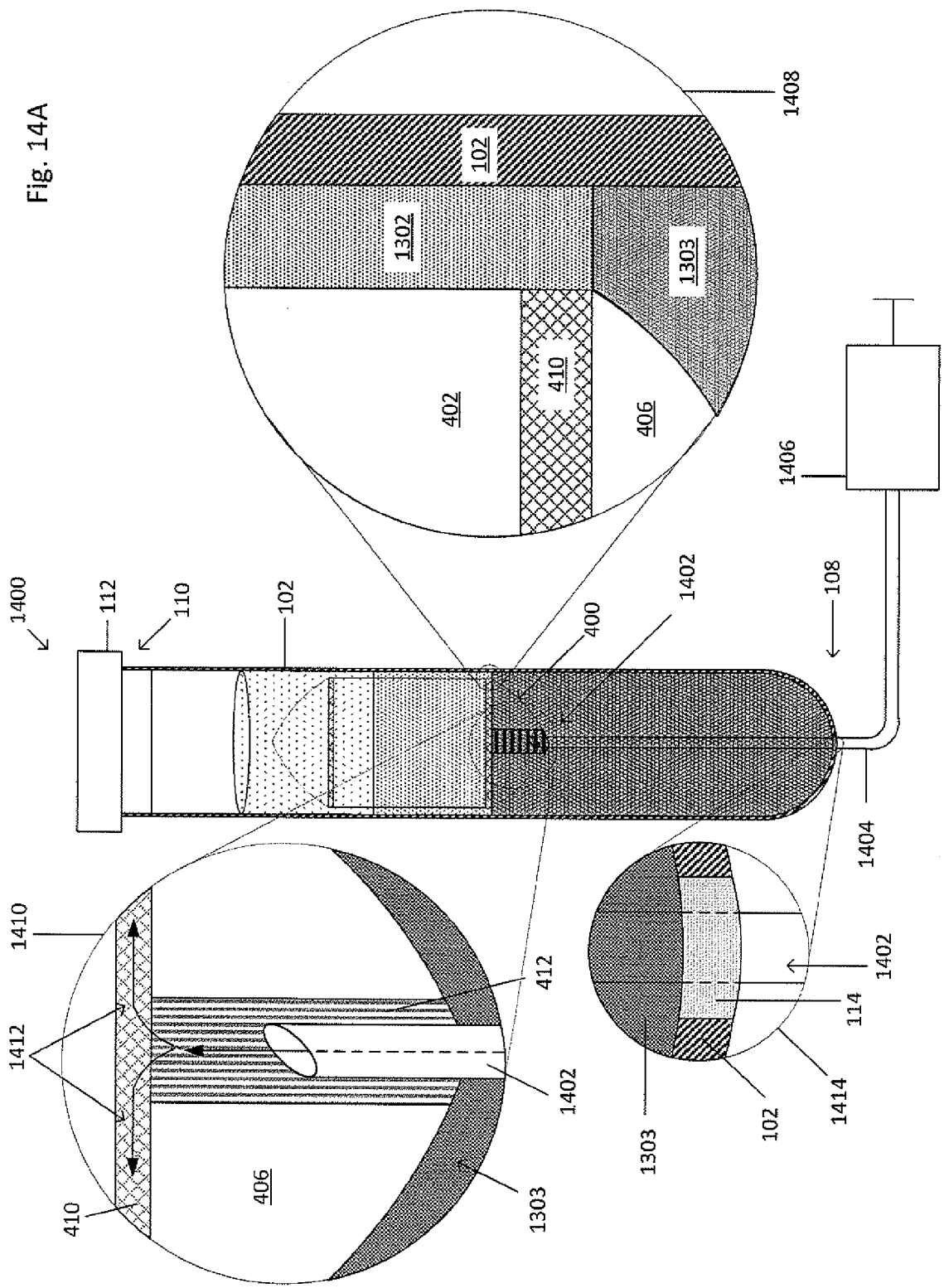

Referring to FIG. 14A, an isometric view of the tube and expandable float system 1400 having undergone density-based separation, such as by centrifugation, is shown. After centrifugation, the expandable float 400 settles within the fractions 1301-1303 based on the density of the expandable float 400 relative to the respective densities of the fractions 1301-1303. For example, the expandable float 400 has a density that causes the expandable portion 410 to settle on top of the densest fraction 1303. To form a seal or trap the target analyte, an expanding fluid may be introduced to the expandable portion 410, thereby causing the expandable portion 410 to radially expand to the sidewall of the tube 102. The needle 1402 may be inserted through a portion of the tube 102, such that the needle 1402 pierces the sidewall of the tube 102 or pierces a plug 114 having already been molded or inserted into the tube 102 to permit the introduction of the needle 1402, as shown in magnified view 1414. The needle 1402, after being inserted into the tube 102, can pierce a pierceable segment of the expandable float 400. The pierceable segment may be a material covering the central area 412 or may be the central area 412 when the central area 412 includes a filler, such as a porous material. The needle 1402 enters the central area 412 and introduces the expanding fluid 1412 into the central area 412. The expanding liquid 1412 flows through a central area 412 and into the expandable portion 410. The needle 1402 may be connected to a container 1406 via tubing 1404. The container 1406 holds the expanding liquid 1412 to be introduced to the expandable float 400. The needle-tubing-container system may be a pump or a syringe. When a pump is used, the pump may be controlled by a program to determine flow rate of the expanding liquid into the tube and expandable float system.

As shown in FIG. 14B, the expandable portion 410, being made of an expandable material, radially expands by absorbing the expanding fluid. The expandable material of the expandable portion 410 absorbs the expanding liquid introduced by the needle 1402 through the central area 412, thereby radially expanding towards the sidewall of the tube 102. The expandable portion 410, as shown in magnified view 1416, can form a seal 1418 with the tube 102 or can trap the target analyte. The seal 1418 can prevent fractions 1302, 1303 from contacting each other. The seal 1418 may also inhibit fluids from flowing past the expandable float 400 in the tube 102.

Figure 15A:
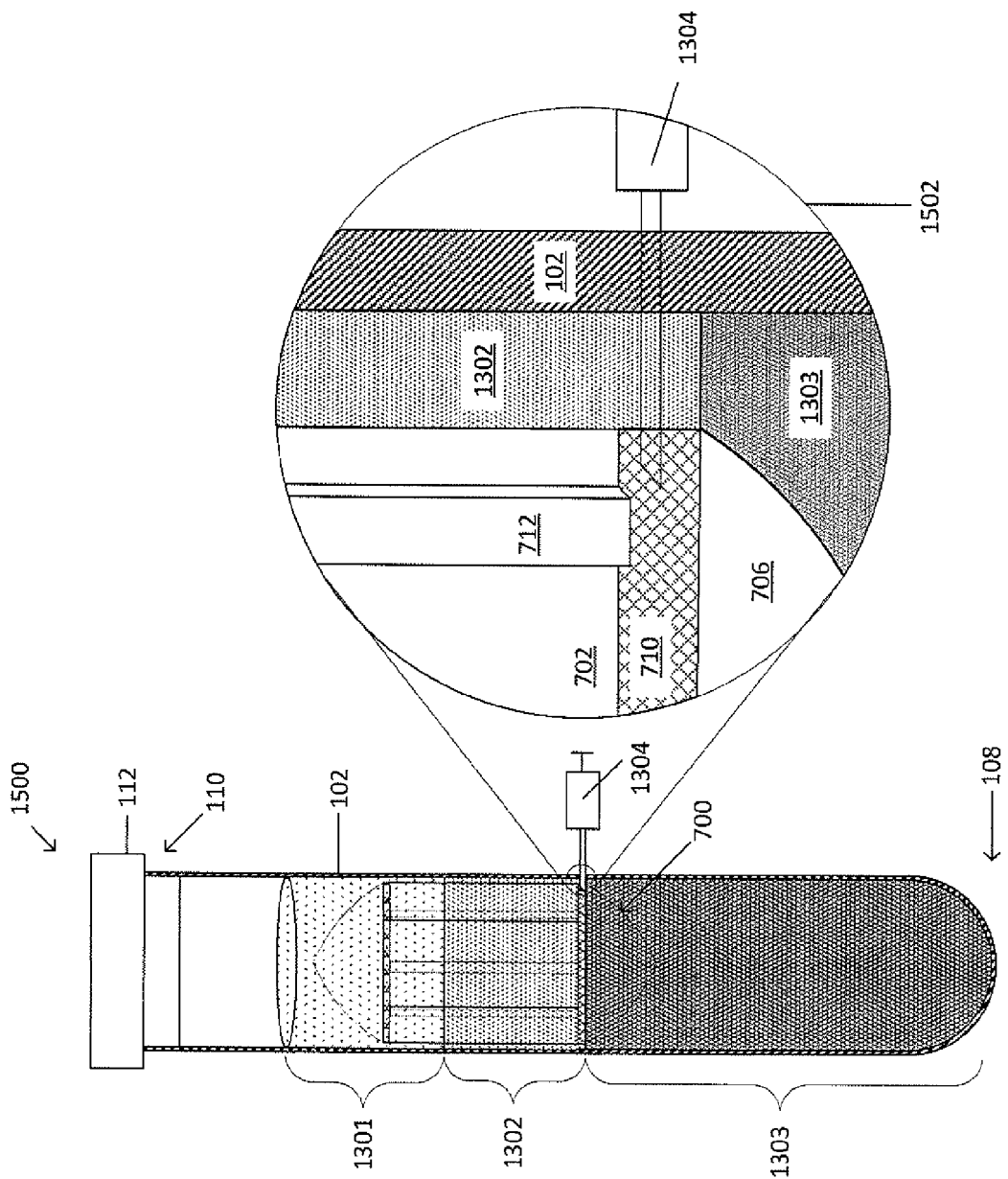
FIGS. 15A-15B show an example system including an expandable float.

Referring now to FIG. 15A, an isometric view of a tube and expandable float system 1500 having undergone density-based separation, such as by centrifugation, is shown. The system 1500 is similar to the system 100 except that the system 1500 includes the expandable float 700 with support members 712 to engage the tube 102. After centrifugation, the expandable float 700 settles within the fractions 1301-1303 based on the density of the expandable float 700 relative to the respective densities of the fractions 1301-1303. The support members 712 engage the tube 102 after centrifugation, effectively capturing the expandable float at an axial position along the tube 102. To form a seal or trap the target analyte, an expanding fluid may be introduced to the expandable portion 710, thereby causing the expandable portion 710 to radially expand to the sidewall of the tube 102. Snapshot 1502 shows a syringe 1304 being used to introduce an expanding fluid to an expandable portion 710 of the expandable float 700. The syringe 1304 can be used to introduce the expanding fluid into the expandable portion 710 of the expandable float 700 through a sidewall of the tube 102. The syringe 1304 may be inserted into the expandable portion 710 of the expandable float 700 through the sidewall of the tube 102 by piercing, creating an opening in the sidewall and inserting the syringe 1004, or the like. The syringe 1304, may, alternatively be a pump. When a pump is used, the pump may be controlled by a program to determine flow rate of the expanding liquid into the tube and expandable float system.

Figure 15B:
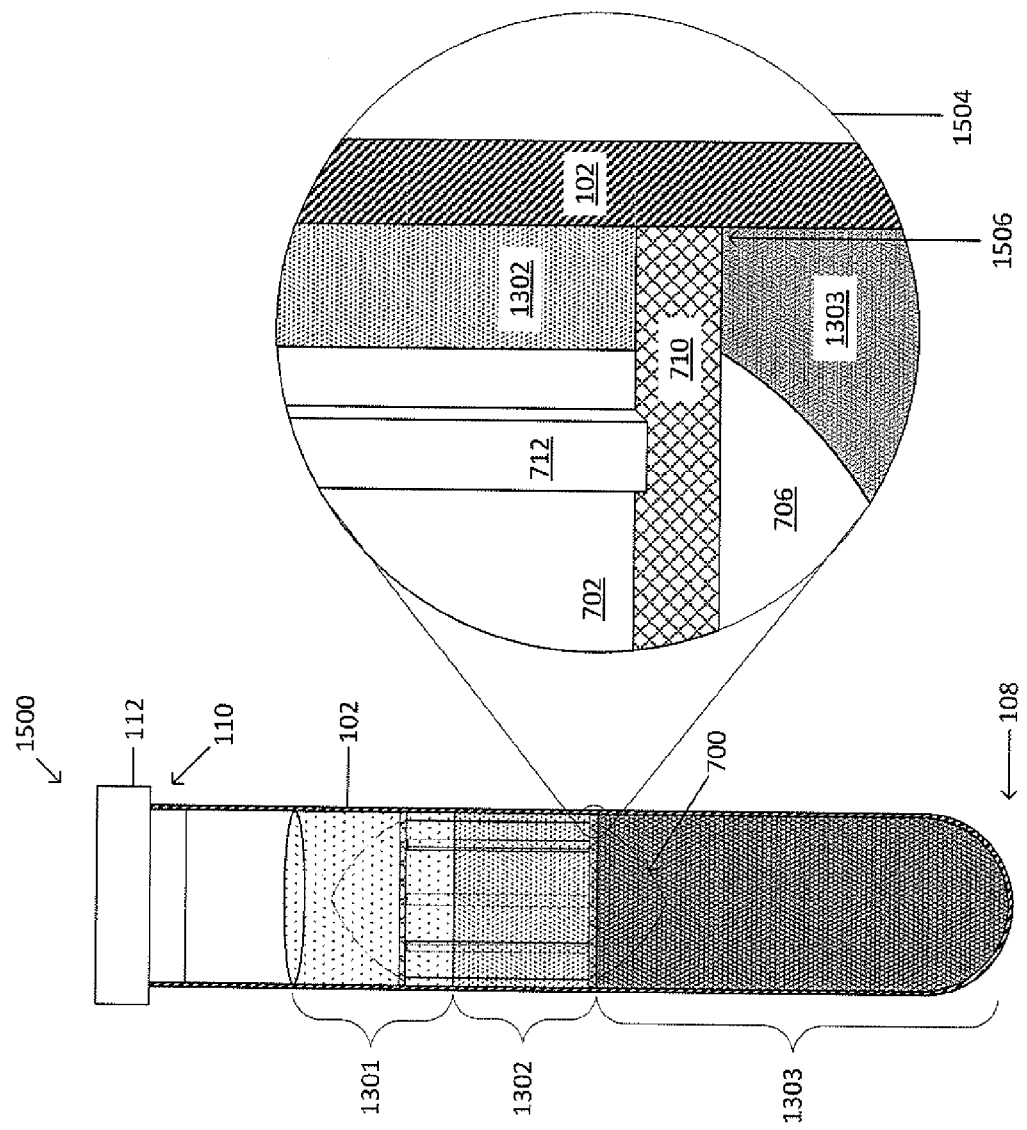

As shown in FIG. 15B, the expandable portion 710, being made of an expandable material, radially expands by absorbing the expanding fluid. The expandable material of the expandable portion 710 absorbs the expanding liquid introduced by the syringe 1304, thereby radially expanding towards the sidewall of the tube 102. The expandable portion 710 can form a seal 1506 with the tube 102 or can trap the target analyte. The seal 1506 can inhibit fractions 1302, 1303 from contacting each other. The seal 1506 may also inhibit fluids from flowing past the expandable float 700 in the tube 102.

Alternatively, the expanding fluid may also be introduced into a system by adding it to the top or bottom of the tube before or after centrifugation. The expandable portion of the expandable float can absorb and retain the expanding fluid, thereby radially expanding to the sidewall of the tube.

Figure 16A:
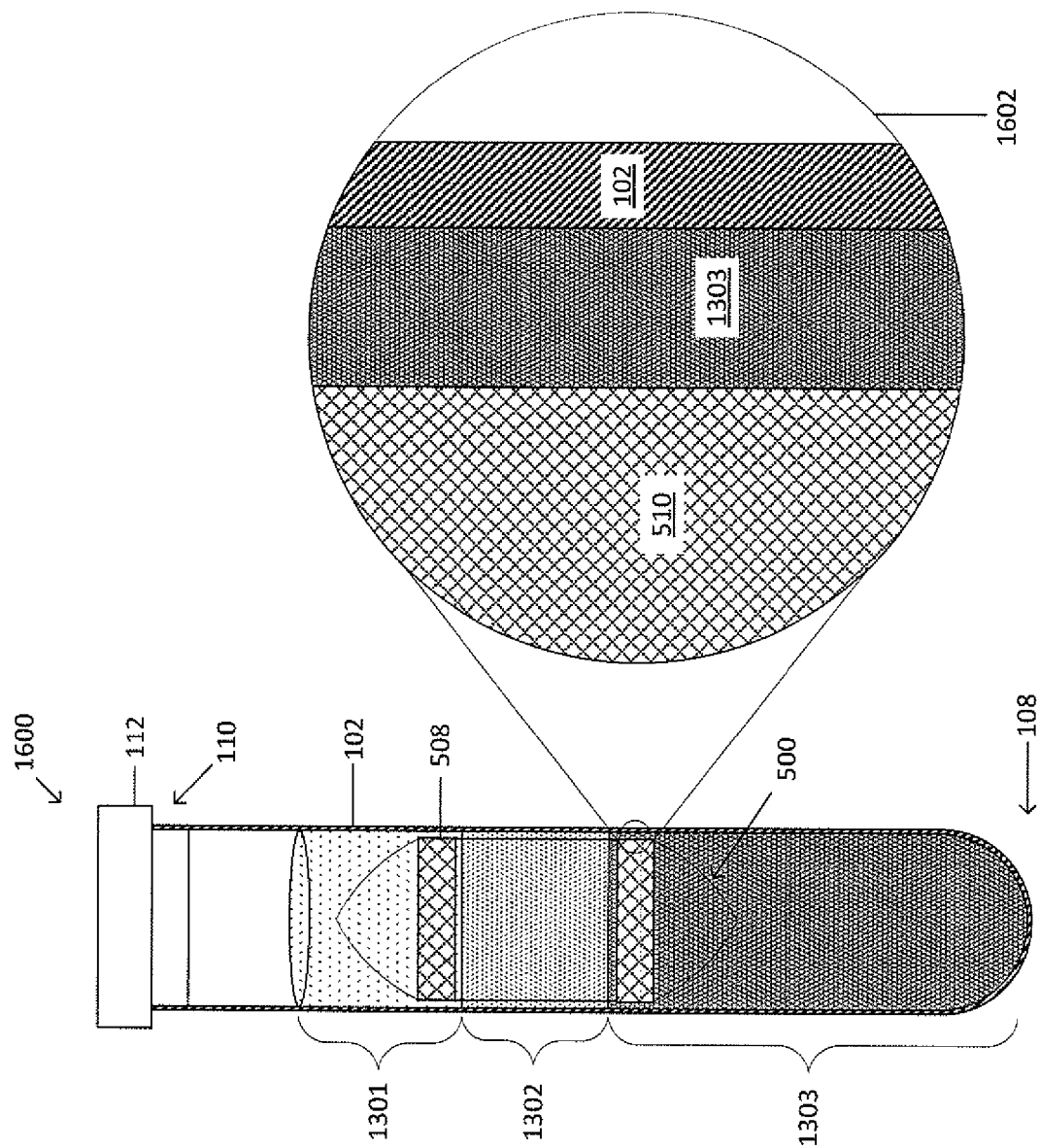
FIGS. 16A-16B show an example system including an expandable float.

Referring now to FIG. 16A, an isometric view of a tube and expandable float system 1600 having undergone density-based separation, such as by centrifugation, is shown. The system 1600 is similar to the system 100 except that the system 1500 includes the expandable float 500 which includes expandable portions 508 and 510 which expand outward due to forces exerted on the expandable portions 508 and 510, such as by a compressive force by end caps 504 and 506. After centrifugation, the expandable float 500 settles within the fractions 1301-1303 based on the density of the expandable float 500 relative to the respective densities of the fractions 1301-1303. To form a seal or trap the target, the expandable portions 508 and 510 undergo a compressive force by the end caps 504 and 506, thereby causing the expandable portions 508 and 510 to expand outward toward the sidewall of the tube 102.

Figure 16B:
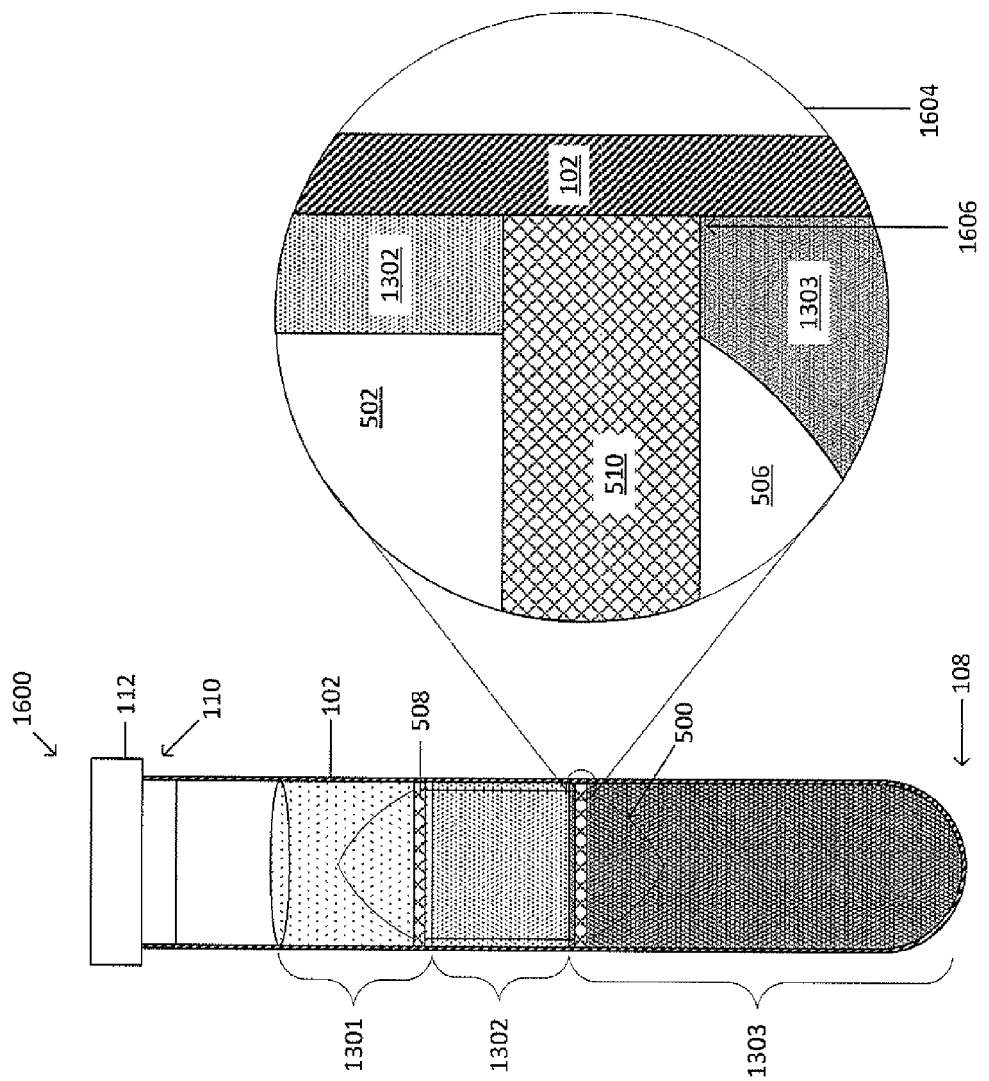

As shown in FIG. 16B, the expandable portions 508 and 510 engage the sidewall of the tube 102, thereby forming seals and capturing the expandable float 500 at the desired location. Snapshot 1604 shows that the expandable portion 510 can form a seal 1606 with the tube 102 or can trap the target analyte between the expandable float 500 and the tube 102. The seal 1606 can inhibit fractions 1302 and 1303 from contacting each other. The seal 1606 may also inhibit fluids from flowing past the expandable float 500 in the tube 102.

Figure 17A:
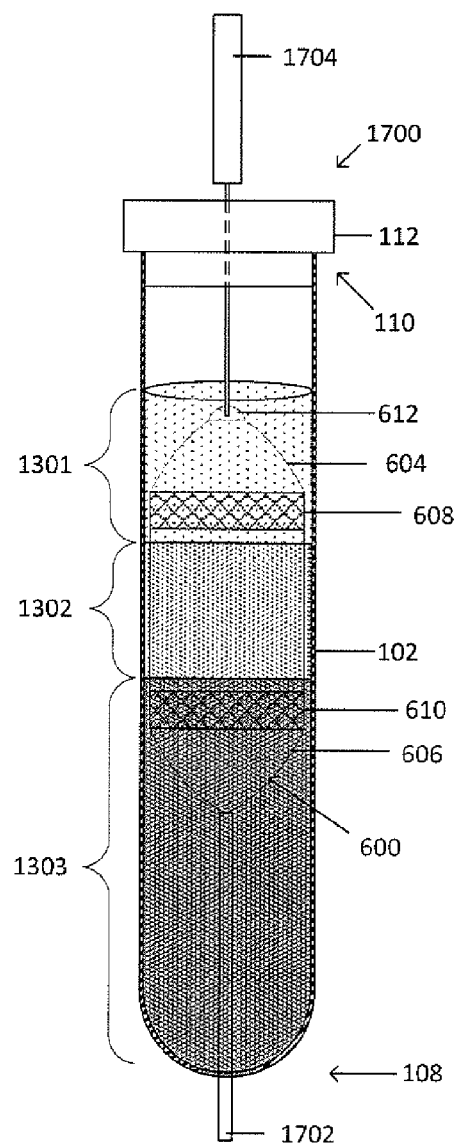
FIGS. 17A-17B show an example system including an expandable float.

Referring now to FIG. 17A, a suspension, suspected of containing a target analyte, undergoes centrifugation. A tube and expandable float system 1700 is similar to system 1600, except that the system 1700 includes an expandable float 600 which includes a fastener 612 to axially compress at least one cap end 604 and 606 to expand the expandable portions 608 and 610 radially. After centrifugation, the expandable float 600 settles within the fractions 1301-1303 based on the density of the expandable float 104 relative to the respective densities of the fractions 1301-1303. To cause the end caps 604 and 606 to exert an axially compressive force on the expandable portions 608 and 610, a tightening device 1704, such as a screwdriver, may engage and tighten the fastener 612. A stabilizer 1702, such as a rod inserted through a plug (not shown) in the bottom end 108 of the tube 102, may engage the opposite side of the expandable float 600 so as to prevent the expandable float 600 from moving within the tube 102 when the tightening device 1704 engages the fastener 612 of the expandable float 600.

Figure 17B:
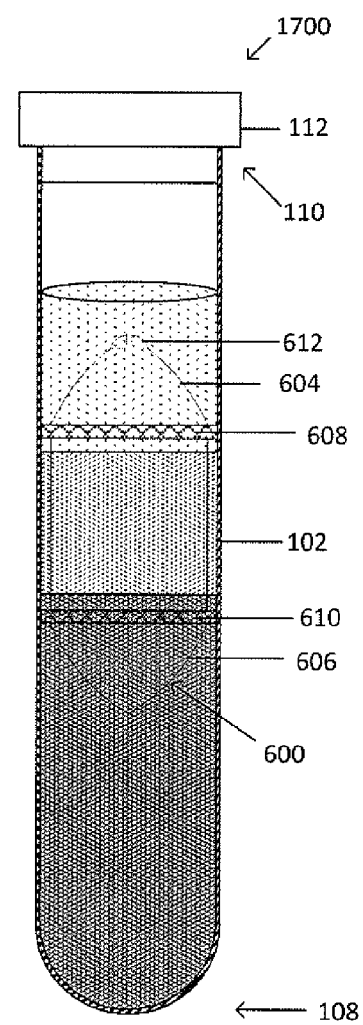

As shown in FIG. 17B, upon tightening the fastener 612, the expandable portions 608 and 610 expand radially due to the axially compressive force by the end caps 604 and 606. The expandable portions 608 and 610 engage the sidewall of the tube 102, thereby forming a seal and capturing the expandable float 600 at the desired location. The seal can inhibit fractions 1302 and 1303 from contacting each other. The seal may also inhibit fluids from flowing past the expandable float 500 in the tube 102.

Figure 18A:
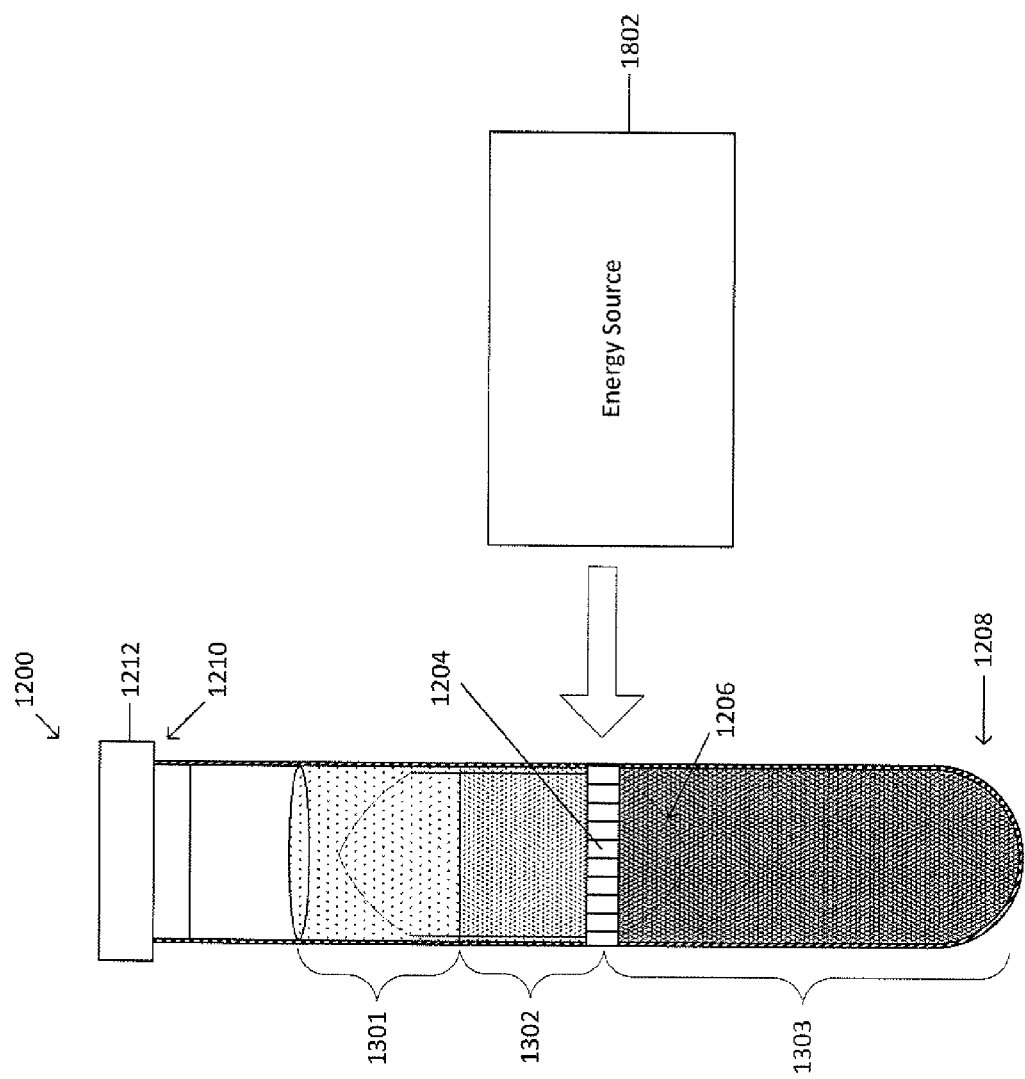
FIGS. 18A-18B show an example system including tube with an expandable portion.

Referring to FIG. 18A, an isometric view of the tube and float system 1200 having undergone density-based separation, such as by centrifugation, is shown. After centrifugation, a float 1206 settles within the fractions 1301-1303 based on the density of the float 1206 relative to the respective densities of the fractions 1301-1303. The float 1206, for example, has a density that is approximately equal to the medium density fraction 1302. To form a seal or trap the target analyte between the float 1206 and the tube 1202, energy may be introduced to an expandable portion 1204 of the tube 1202 by an energy source 1802 to convert or activate the expandable portion 1204. The expandable portion 1204 expands inwardly, thereby reducing an inner diameter of the tube 1202 at the location of the expandable portion 1204 from a first inner diameter to a second inner diameter, such that the second inner diameter is smaller than the first inner diameter.

Figure 18B:
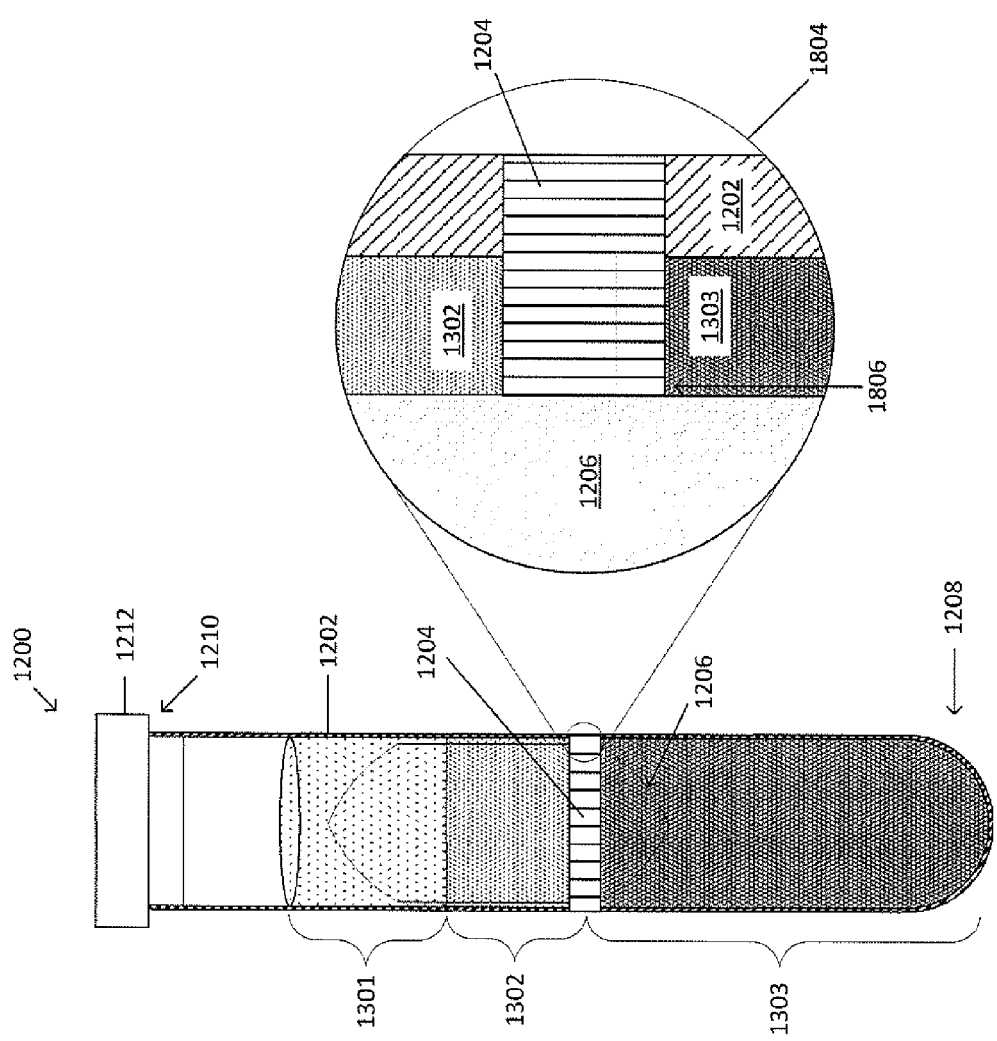

As shown in FIG. 18B, the expandable portion 1204, being made of an expandable material, expands inwardly by converting or activating through the absorption of the energy emitted by the energy source. The expandable portion 1204 can form a seal 1806 with the float 1206 or can trap the target analyte between the float 1206 and the tube 1202. The seal 1806 can prevent fractions 1302 and 1303 from contacting each other. The seal 1806 may also inhibit fluids from flowing past the float 1206.

Alternatively, when the expandable portion of the tube is a piezoelectric material, applying an electrical potential to the expandable portion causes the expandable portion to produce a mechanical strain (i.e. expandable portion expands when an electric potential is applied). The electric potential may be applied by connecting a battery or other power source to the piezoelectric material via leads. Alternatively, the expandable portion may be composed of a shape metal allow to expand (and constrict) based on ambient temperature.

Expansion of the expandable portion may be reversed from the second inner diameter back to the first inner diameter or to a diameter between the first and second inner diameters. The reversal may occur by reversing a mechanism by which the expandable portion was initially expanded, such as by removing the expansion fluids or by removing the mechanical force, by introducing a constriction fluid (i.e. a fluid to reverse the effects of the expanding fluid), by puncturing the expandable portion, by introducing at least one form of energy, or by any appropriate mechanism for constricting the expandable portions.

II. Extraction

FIG. 19A shows an example of a system 1900 for extracting the high-density fraction 1303. The system 1900 includes an extraction device 1902, such as a needle or the like, connected to a receptacle 1906, such as a tube, a vacuum tube, or the like, via tubing 1904. The extraction device 1902 punctures a plug (not shown) of the tube 102. As described above, the plug (not shown) is composed of a rubber that enables the needle 1902 to pass through while forming a liquid-tight seal around the needle 1902 to prevent the liquid contents from leaking around the needle 1902. A pressure gradient, such as created by a vacuum, then causes the high-density fraction 1303 and other materials and fluids trapped below the expandable float 104 to be drawn through the tubing 1904 into the receptacle 1906. A second needle (not shown) may be used to flow in fluids, such as perfluoroketones, fluorinated ketones, hydrofluoroethers, hydrofluorocarbons, perfluorocarbons, phosphate buffered saline or air, to replace the volume of the removed volume of the high-density fraction 1303. The high-density fraction 1303 and other materials and fluids trapped below the expandable float 104 are drawn into the receptacle 1906. When the needle 1902 is removed, the opening in the plug (not shown) created by the needle 1902 closes to form a liquid-tight seal. The needle-tubing-container system may, alternatively, be a pump or a syringe. When a pump is used, the pump may be controlled by a program to determine flow rate of the high-density fraction 1303 out of the tube and expandable float system.

Figure 19B:
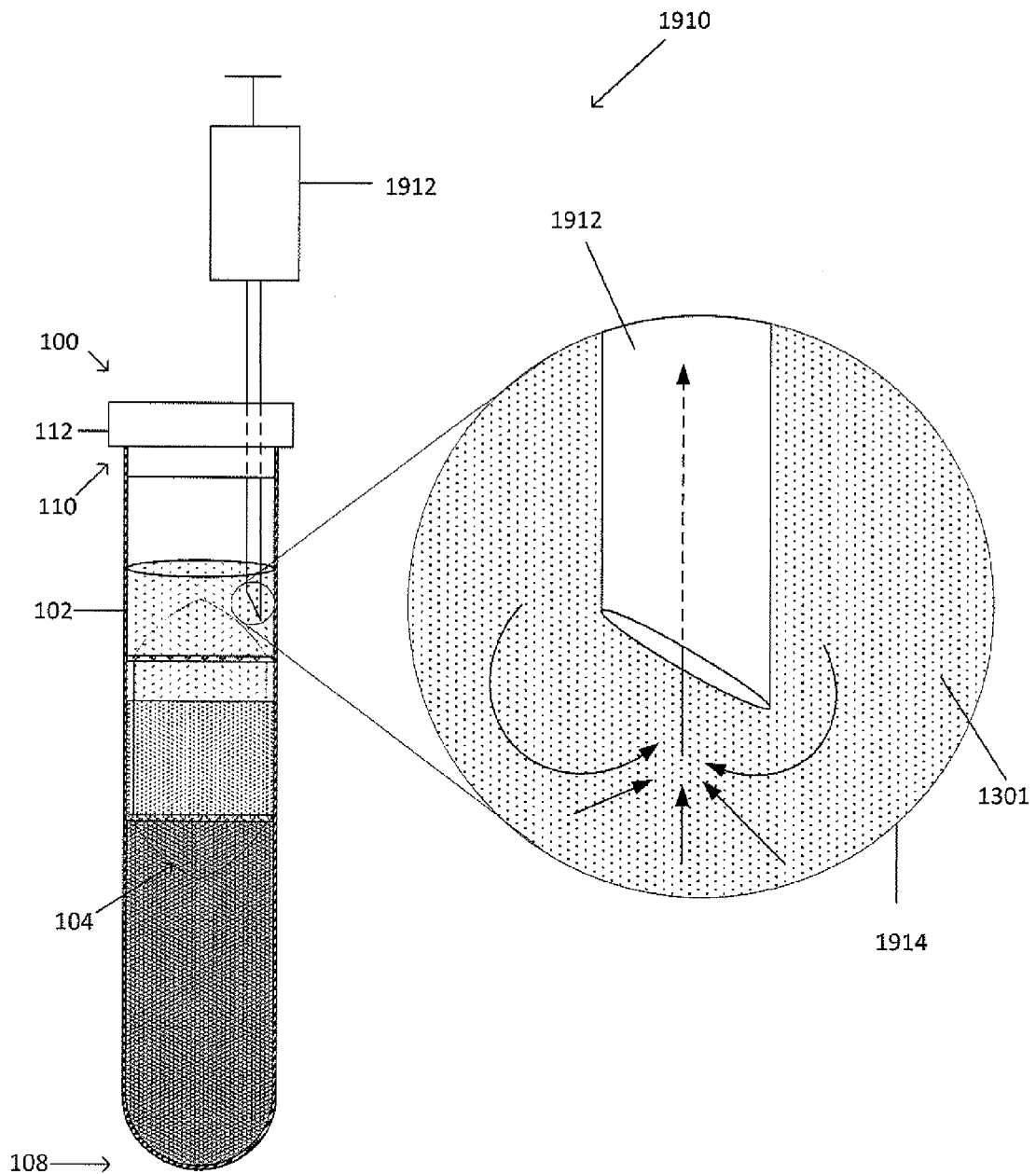

FIG. 19B shows an example of a system 1910 for extracting the low-density fraction 1301. The system 1910 includes an extraction device 1912, such as a syringe, needle, or the like. The extraction device 1912 may puncture the cap 112 of the tube 102 or the cap 112 may be removed, thereby inserting the extraction device 1912 directly into the tube 102. A pressure gradient or suction causes the low-density fraction 1301 and other materials and fluids trapped above the expandable float 104 to be drawn into the extraction device 1912. The extraction device 1912 may be a pump or a syringe. When a pump is used, the pump may be controlled by a program to determine flow rate of the low density fraction 1301 being extracted from the system.

Figure 19C:
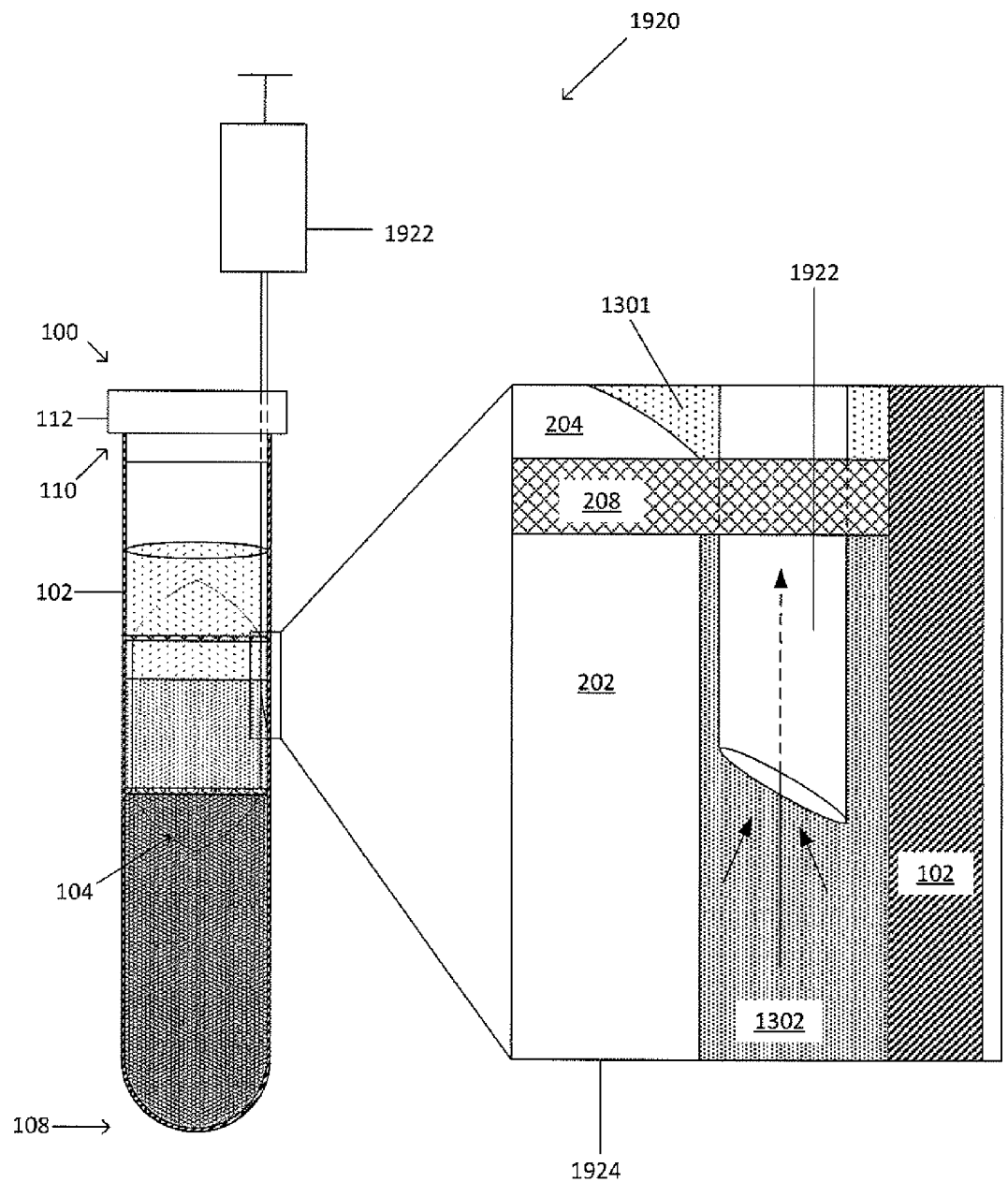

FIG. 19C shows an example of a system 1920 for extracting a medium-density fraction 1302. The system 1920 is similar to the system 1910 except that the extraction device 1922 has a needle long enough to get into the medium-density fraction 1302 by puncturing the expandable portion 608 of the expandable float 104. A pressure gradient or suction causes the medium density fraction 1302 to be drawn into the extraction device 1922. The extraction device 1922 may be a pump or a syringe. When a pump is used, the pump may be controlled by a program to determine flow rate of the medium density fraction 1302 being extracted from the system.

FIG. 19D shows an example of a system 1930 for extracting a medium-density fraction 1302. The system 1930 is similar to the system 1910 except that the extraction device 1932 has a needle to get into the medium-density fraction 1302 by puncturing the sidewall of the tube 102, the medium-density fraction 1302 being located between the expandable float 104 and the sidewall of the tube 102. A pressure gradient or suction causes the medium density fraction 1302 to be drawn into the extraction device 1934. The extraction device 1934 may be a pump or a syringe. When a pump is used, the pump may be controlled by a program to determine flow rate of the medium density fraction 1302 being extracted from the system.

It should be understood that the method and system described and discussed herein may be used with any appropriate suspension or biological sample, such as blood, bone marrow, cystic fluid, ascites fluid, stool, semen, cerebrospinal fluid, nipple aspirate fluid, saliva, amniotic fluid, vaginal secretions, mucus membrane secretions, aqueous humor, vitreous humor, vomit, and any other physiological fluid or semi-solid. It should also be understood that a target analyte can be a cell, such as ova or a circulating tumor cell ("CTC"), a circulating endothelial cell, a vesicle, a liposome, a protein, a nucleic acid, a biological molecule, a naturally occurring or artificially prepared microscopic unit having an enclosed membrane, parasites, microorganisms, or inflammatory cells.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

We claim:

1. A float for separating a suspension, the float comprising:
a main body having a top end and a bottom end; and,
at least one band composed of a piezoelectric material,
wherein the at least one band extends at least partially circumferentially around the main body,
wherein the at least one band has a first phase and a second phase,
wherein the at least one band expands from the first phase to the second phase,
wherein the at least one band does not expand from the first phase to the second phase upon exposure to the suspension or suspension components, and,
wherein the at least one band does not expand from the first phase to the second phase upon the introduction of a centrifugal force.

2. The float of claim 1, wherein the piezoelectric material is connected to a power source to supply an electric potential via at least one lead.

3. A float for separating a suspension, the float comprising:
a main body having a top end and a bottom end; and,
at least one band composed of a shape metal alloy,
wherein the at least one band extends at least partially circumferentially around the main body,
wherein the at least one band has a first phase and a second phase,
wherein the at least one band expands from the first phase to the second phase,
wherein the at least one band does not expand from the first phase to the second phase upon exposure to the suspension or suspension components, and,
wherein the at least one band does not expand from the first phase to the second phase upon the introduction of a centrifugal force.

* * * * *